(12) United States Patent
Hong et al.

(10) Patent No.: US 9,808,560 B2
(45) Date of Patent: Nov. 7, 2017

(54) BIODEGRADABLE, NON-THROMBOGENIC ELASTOMERIC POLYURETHANES

(71) Applicant: University of Pittsburgh—Of the Commonwealth System of Higher Education, Pittsburgh, PA (US)

(72) Inventors: Yi Hong, Irving, TX (US); William R Wagner, Gibsonia, PA (US); Sang-Ho Ye, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 134 days.

(21) Appl. No.: 14/194,188

(22) Filed: Feb. 28, 2014

(65) Prior Publication Data

US 2014/0248232 A1 Sep. 4, 2014

Related U.S. Application Data

(60) Provisional application No. 61/771,484, filed on Mar. 1, 2013.

(51) Int. Cl.
| | |
|---|---|
| A61K 31/74 | (2006.01) |
| A61L 33/06 | (2006.01) |
| A61L 27/18 | (2006.01) |
| A61L 27/58 | (2006.01) |
| A61L 31/10 | (2006.01) |
| A61L 31/16 | (2006.01) |

(52) U.S. Cl.
CPC ............. *A61L 33/068* (2013.01); *A61L 27/18* (2013.01); *A61L 27/58* (2013.01); *A61L 31/10* (2013.01); *A61L 31/16* (2013.01); *A61L 33/064* (2013.01); *A61L 2300/402* (2013.01); *A61L 2300/404* (2013.01); *A61L 2300/41* (2013.01); *A61L 2300/416* (2013.01)

(58) Field of Classification Search
CPC .. A61L 33/068; A61L 27/18; A61L 2300/416; A61L 2300/41; A61L 2300/404; A61L 2300/402; A61L 33/064; A61L 27/58; A61L 31/10; A61L 31/148; A61L 31/16; C08L 67/04
See application file for complete search history.

(56) References Cited

U.S. PATENT DOCUMENTS

| | | | |
|---|---|---|---|
| 3,673,158 A | 6/1972 | Reder | |
| 5,401,571 A | 3/1995 | Shiraki | |
| 5,541,251 A * | 7/1996 | Bontinck | C09D 133/062 524/501 |
| 7,833,544 B2 | 11/2010 | Lewis | |
| 7,879,444 B2 | 2/2011 | Jiang | |
| 8,628,761 B2 | 1/2014 | Adhikari | |
| 2008/0014244 A1 * | 1/2008 | Gale | A61L 31/06 424/426 |
| 2010/0179284 A1 * | 7/2010 | Ward | A61K 31/785 525/54.2 |

FOREIGN PATENT DOCUMENTS

| | | |
|---|---|---|
| WO | 2004009227 A2 | 1/2004 |
| WO | 2010065960 A2 | 6/2010 |

OTHER PUBLICATIONS

Hong et al ("A small diameter, fibrous vascular conduit generated from a poly(ester urethane)urea and phospholipid polymer blend," Biomaterials vol. 30, Issue 13, May 2009, pp. 2457-2467; Available online Feb. 1, 2009).*
Ishihara et al ("Synthesis of phospholipid polymers having a urethane bond in the side chain as coating material on segmented polyurethane and their platelet adhesion-resistant properties," Biomaterials 16 (19958) 873-879)).*
Hasegawa et al ("Preparation and performance of protein-adsorption-resistant asymmetric porous membrane composed of polysulfone/phospholipid polymer blend," Biomaterials, 22 (2001), pp. 243-251).*
Of Guan et al ("Synthesis, characterization, and cytocompatibility of elastomeric, biodegradable poly(ester-urethane)ureas based on poly(caprolactone) and putrescine," J Biomed Mater Res, 61 (2002), pp. 493-503).*
Cao, Jun et al.; Synthesis of a Novel Biodegradable Polyurethane with Phosphatidylcholines; Int. J. Mol. Sci. 2010, 11, 1870-1877.
Tan, Dongsheng et al.; Double-chain phospholipid end-capped polyurethanes: Synthesis, characterization and platelet adhesion study, Applied Surface Science, 2012 2697-2760. Available online Nov. 2, 2011.
Wang, Zhigao et al.; Synthesis and micellization of new biodegradable phosphorylcholine—capped polyurethane, Journal of Polymer Science Part A: Polymer Chemistry, 2011, 49, 2033-2042.
Lipatova, T. E. et al., Biocompatible polymers for medical application, Macromol. Symp.152, 139-150 (2000).

* cited by examiner

*Primary Examiner* — Suzanne Ziska
(74) *Attorney, Agent, or Firm* — Bartony & Associates, LLC

(57) ABSTRACT

A method of forming an implantable article includes providing a biodegradable polymer including anti-thrombogenic groups along the length of the biodegradable polymer, biodegradable groups in the backbone of the biodegradable polymer and a plurality of functional groups adapted to react with reactive functional groups on a surface of the implantable article, and reacting at least a portion of the plurality of functional groups with the reactive functional groups on the surface of the implantable article.

29 Claims, 15 Drawing Sheets

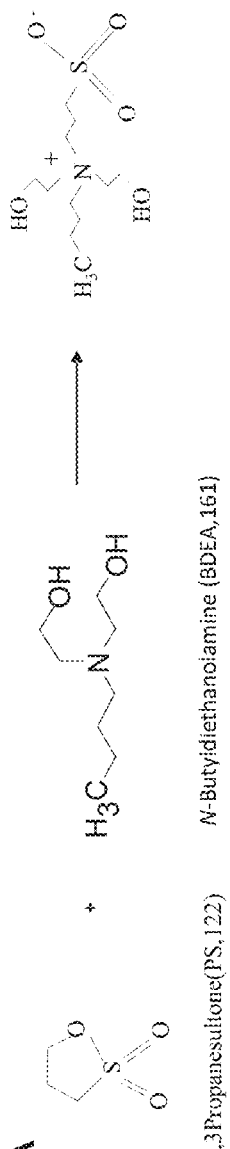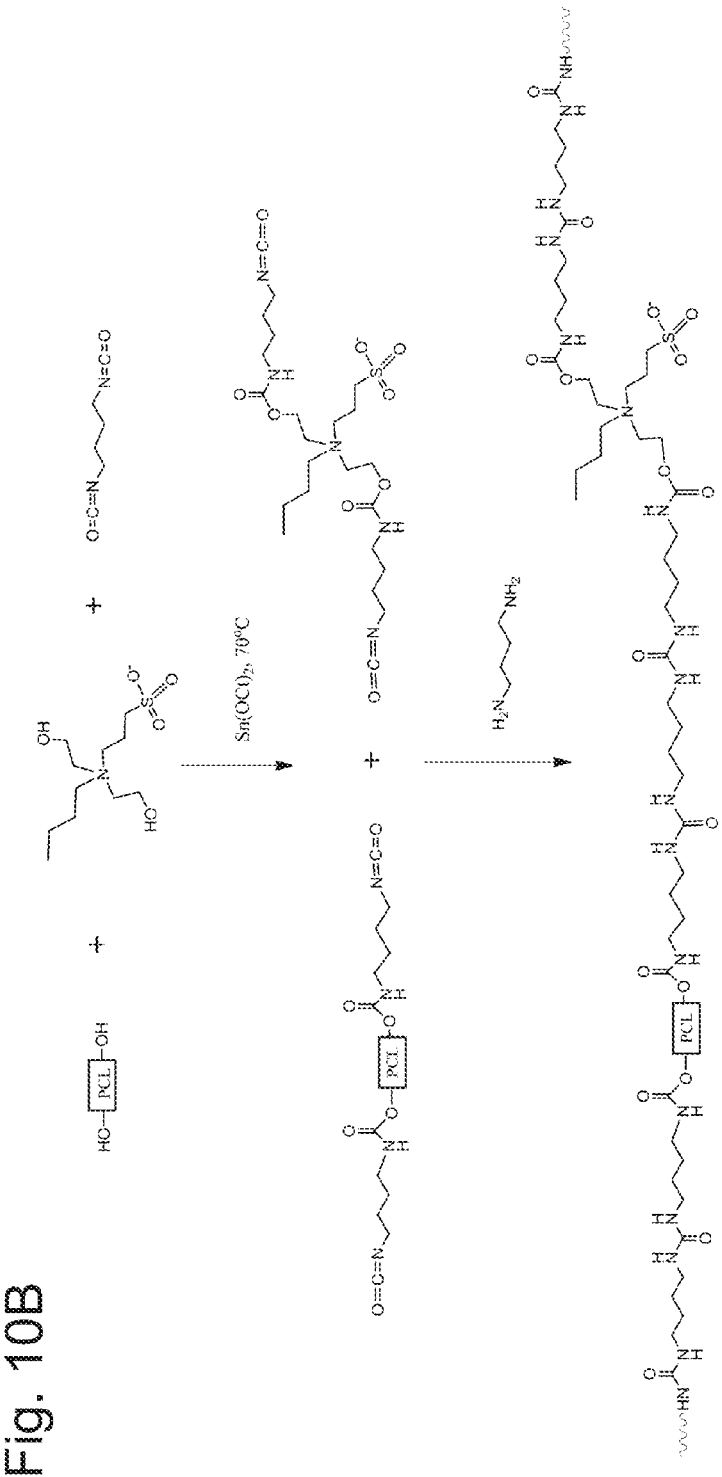
Fig. 10A
Fig. 10B

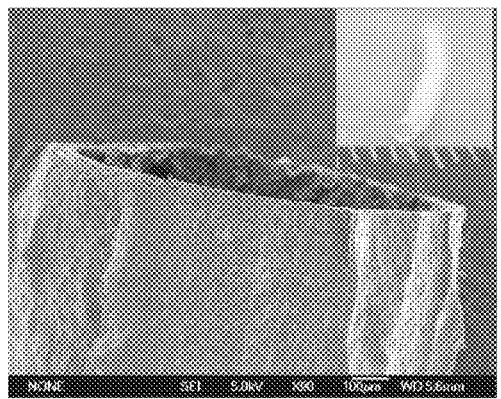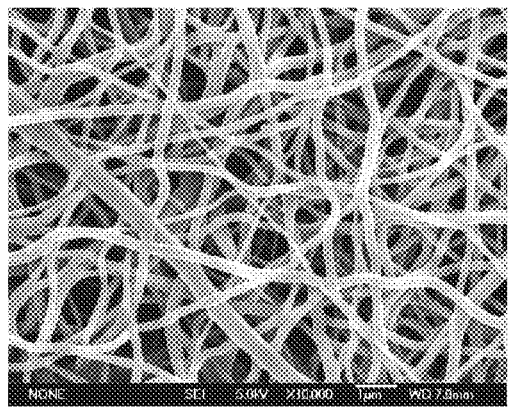
Fig. 17A　　　　　　　　　　Fig. 17B
PCSUU 100/0　　　　　　　PCSUU 25/75
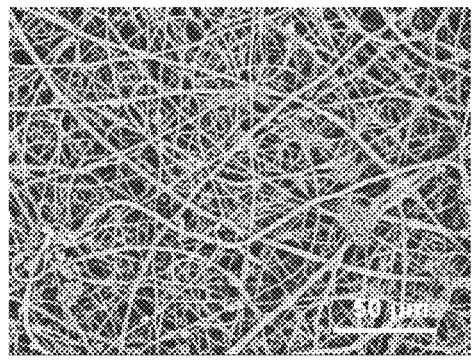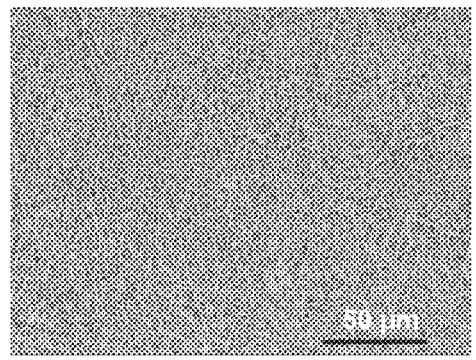
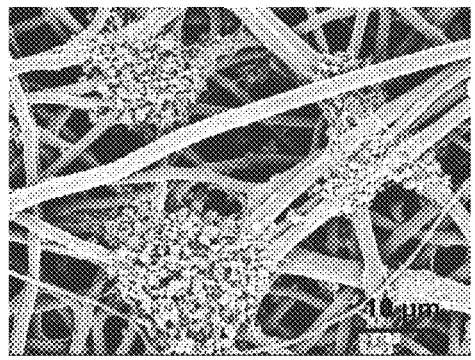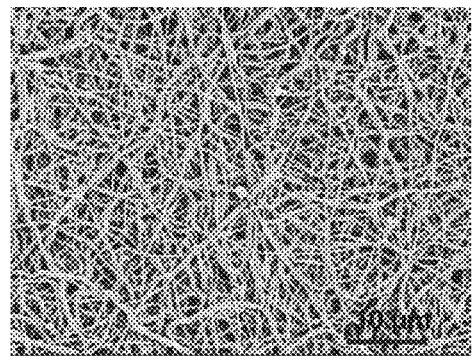
Fig. 18A　　　　　　　　　　Fig. 18B

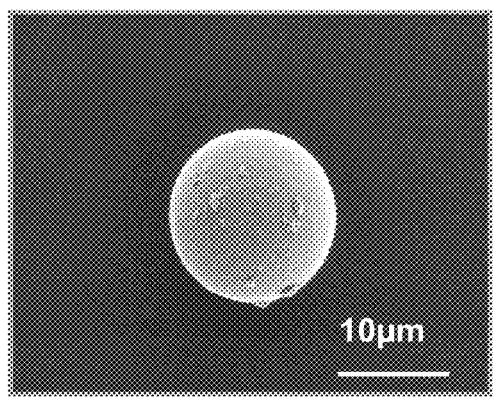 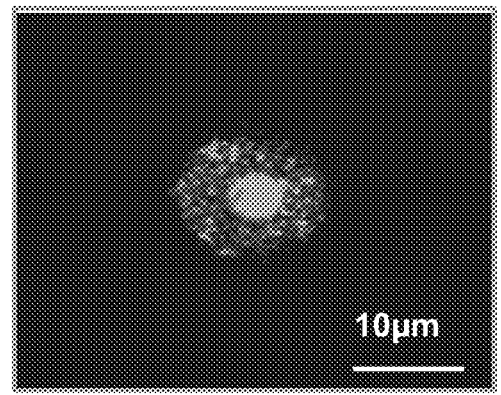
Fig. 23A    Fig. 23B
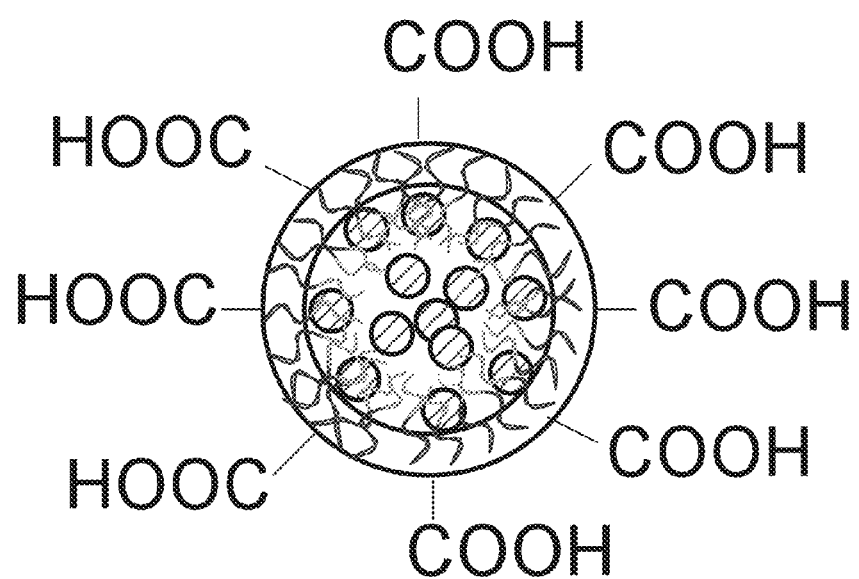
Fig. 24

BIODEGRADABLE, NON-THROMBOGENIC ELASTOMERIC POLYURETHANES

CROSS-REFERENCE TO RELATED APPLICATIONS

This application claims benefit of U.S. Provisional Patent Application Ser. No. 61/771,484, filed Mar. 1, 2013, the disclosure of which is incorporated herein by reference.

GOVERNMENTAL INTEREST

This invention was made with government support under grant no. EEC-0812348 awarded by the National Science Foundation Engineering Research Center. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

The term "thrombogenicity" refers to the tendency of a material in contact with blood to produce a clot or thrombus. The term refers to both fixed thrombi and to emboli (which are thrombi which have become detached and travel through the bloodstream). The term "thrombogenicity" also encompasses events such as the activation of immune pathways and the complement system. Thrombosis and intimal hyperplasia are, for example, considered to be two primary reasons to result in implantation failure of implantable devices such as implantable vascular devices, including metallic stents and vascular grafts. Intimal hyperplasia is the thickening of the intima or innermost layer of a blood vessel as a complication of a procedure. It is a response of the vessel to injury. There have been a number of attempts at synthesizing "non-thrombogenic" implantable articles and devices, but problems persist.

For example, a number of current drug eluting vascular stents employ non-degradable polymers as drug reservoirs. Drug eluting stents exhibit reduced restenosis rates, and have gained market share as a result of their improved efficacy over non-coated stents. A problem associated with non-degradable polymeric coatings is the thrombogenicity encountered on those surfaces, which has been of particular concern later in the implant period, when anti-thrombotic management may not be as aggressive. Late stent thrombosis, where patients develop thrombotic complications much later than the normal early risk period, have been attributed to the tendency of these stents not to become endothelialized while presenting a relatively thrombogenic surface to the blood. While stents with biodegradable coatings generally appear to perform similarly to those with nondegradable coatings, there is little evidence that the biodegradable coatings employed to date have achieved marked reduction in thrombotic complication rates.

SUMMARY

In one aspect, a method of forming an implantable article includes providing a biodegradable polymer including anti-thrombogenic groups along the length of the biodegradable polymer, biodegradable groups in the backbone of the biodegradable polymer and a plurality of functional groups adapted to react with reactive functional groups on a surface of the implantable article, and reacting at least a portion of the plurality of functional groups with (at least a portion of) the reactive functional groups on the surface of the implantable article. The biodegradable groups may, for example, include at least one hydrolytically labile bond. In a number of embodiments, the biodegradable groups include at least one of ester groups, orthoester groups, thioether-ester groups, anhydride groups, amide groups (for example, peptide groups), carbonate groups. In a number of embodiments, the biodegradable groups include ester groups.

In a number of embodiments, the anti-thrombogenic groups are zwitterionic groups. The zwitterionic group may for example include at least one of a phosphorylcholine group, a derivative of a phosphorylcholine group, a sulfobetaine group, a derivative of a sulfobetaine group, a carboxybetaine group, or a derivative of a carboxybetaine group.

The biodegradable polymer may, for example, be an elastomer such as a thermoplastic elastomer. In a number of embodiments, the biodegradable polymer includes urethane and/or urea linkages. In a number of embodiments, the biodegradable polymer is a polyurethane or a polyurethane urea including soft segments.

The biodegradable polymer may, for example, be formed by first forming a precursor polymer via the reaction of:
  (a) a multi-functional active hydrogen component including a polymer having multiple active hydrogen functional groups and biodegradable groups in the backbone thereof and at least one compound including multiple active hydrogen functional groups and at least one of the plurality of functional groups, and
  (b) a multi-functional isocyanate component; and
reacting the precursor polymer with a compound including at least one zwitterionic group and a functional group reactive with one of the plurality of functional groups. The polymer includes multiple active hydrogen functional groups and biodegradable groups in the backbone thereof may, for example, be a polyester. The multi-functional isocyanate component can include a single multi-functional isocyanate compound, or a blend of different multi-functional isocyanate compounds.

The biodegradable polymer may, for example, be formed via the reaction of a multi-functional active hydrogen component including a polymer having multiple active hydrogen functional groups and biodegradable groups in the backbone thereof, at least one compound including multiple active hydrogen functional groups and at least one of the plurality of functional groups and a compound including at least one zwitterionic group and multiple active hydrogen functional groups with a multi-functional isocyanate component. As described above, the polymer including multiple active hydrogen functional groups and biodegradable groups in the backbone thereof may, for example, be a polyester.

At least one of the plurality of functional groups of the biodegradable polymer may, for example, be at least one of a carboxyl group, an amine group, a thiol group, an alkyl siloxane group. In a number of embodiments, the plurality of functional groups of the biodegradable polymer include carboxyl groups.

The biodegradable polymer may, for example, be adapted to form microparticles. In a number of embodiments, a portion of the plurality of functional groups of the biodegradable polymer are reacted with a crosslinking compound including at least two functional groups reactive with at least two of the plurality of functional groups of the biodegradable polymer after the microparticles are formed. In a number of embodiments, the crosslinking compound is a compound of relatively low molecular weight including two functional groups reactive with two of the plurality of functional groups of the biodegradable polymer.

The implantable article is a stent and the biodegradable polymer is a coating on the stent or a scaffold for tissue engineering.

The biodegradable polymer may, for example, further include a biologically active compound releasably loaded within the biodegradable polymer. In a number of embodiments, the biologically active agent is selected from the group consisting of an anti-proliferative agent, an antibiotic, an antiviral, an antimycotic, an anticancer agent, an immunosuppressant, a chemotherapeutic agent, an anti-rejection agent, an analgesic agent, and an anti-inflammatory agent. In a number of embodiments, the biologically active agent is an anti-proliferative agent.

In another aspect, an implantable article includes a biodegradable polymer including anti-thrombogenic groups along the length of the biodegradable polymer and biodegradable groups in the backbone thereof (as, for example, described above). The biodegradable polymer is covalently bonded to a surface of the implantable article.

In other aspects, methods of forming the biodegradable polymers including anti-thrombogenic groups along the length of the biodegradable polymer and biodegradable groups in the backbone thereof are provided. In still other aspect, biodegradable polymers as described above are provided. Biodegradable polymers hereof may, for example, include anti-thrombogenic groups along the length of the biodegradable polymer, biodegradable groups in the backbone of the biodegradable polymer and a plurality of functional groups as described above. Such functional groups may, for example, include at least one of a carboxyl group, an amine group, a thiol group, or an alkyl siloxane group. The biodegradable polymers may, for example, from microparticles as described herein.

In a further aspect, a method includes providing a biodegradable polymer including zwitterionic groups and a plurality of functional groups, forming a microparticle with the biodegradable polymer, and crosslinking at least a portion of the functional groups of the biodegradable polymer by via a crosslinking compound including at least two functional groups reactive with at least two of the plurality of functional groups of the biodegradable polymer. A portion of the plurality of functional groups of the biodegradable polymer may, for example, remain (unreacted) after crosslinking. The portion of the plurality of functional groups are adapted to react with reactive functional groups on a surface to tether the microparticle to the surface. The microparticle may, for example, be formed by placing the biodegradable polymer in a solution including a surfactant.

The biodegradable groups may, for example, include at least one hydrolytically labile bond. The biodegradable groups of the biodegradable polymer may, for example, include at least one of ester groups, orthoester groups, thioether-ester groups, anyhydride groups, amide groups (for example, peptide groups), or carbonate groups. In a number of embodiments, the biodegradable groups include ester groups. The zwitterionic groups may, for example, be selected from the group consisting of phosphorylcholine groups, derivatives of a phosphorylcholine groups, a sulfobetaine groups, derivative of a sulfobetaine groups, carboxybetaine groups, or derivative of carboxybetaine groups.

The biodegradable polymer may, for example, be an elastomer such as a thermoplastic elastomer. In a number of embodiments, the biodegradable polymer includes urethane and/or urea linkages. The biodegradable polymer may, for example, be a polyurethane or a polyurethane urea including soft segments.

In a number of embodiments, the biodegradable polymer is formed by first forming a precursor polymer via the reaction of:
  (a) a multi-functional active hydrogen component including a polyester having multiple active hydrogen functional groups and at least one compound including multiple active hydrogen functional groups and at least one of the plurality of functional groups, and
  (b) a multi-functional isocyanate component; and
reacting the precursor polymer with a compound including at least one zwitterionic group and a functional group reactive with one of the plurality of functional groups.

In a number of embodiments, the biodegradable polymer if formed via the reaction of a multi-functional active hydrogen component including a polyester having multiple active hydrogen functional groups, at least one compound including multiple active hydrogen functional groups and at least one of the plurality of functional groups and a compound including at least one zwitterionic group and multiple active hydrogen functional groups with a multi-functional isocyanate component.

At least one of the functional groups of the biodegradable polymer may, for example, be selected from the group consisting of a carboxyl group, an amine group, a thiol group, an alkyl siloxane group. In a number of embodiments, at least one of the functional groups of the biodegradable polymer is a carboxyl group.

The method may, for example, further include loading a biologically active agent into a void of the microparticle. The biologically active agent may, for example, be selected from the group consisting of an anti-proliferative agent, an antibiotic, an antiviral, an antimycotic, an anticancer agent, an immunosuppressant, a chemotherapeutic agent, an anti-rejection agent, an analgesic agent, and an anti-inflammatory agent. In a number of embodiments, the biologically active agent is an anti-proliferative agent.

As described above, the at least one zwitterionic group may, for example, be selected from the group consisting of a phosphorylcholine group, a derivative of a phosphorylcholine group, a sulfobetaine group, a derivative of a sulfobetaine group, a carboxybetaine group, or a derivative of a carboxybetaine group.

The microparticle may, for example, be formed by dispersing the biodegradable polymer in a solution including a surfactant.

In still a further aspect, microparticle includes a biodegradable polymer including zwitterionic groups as, for example, described above. The microparticle includes a void therein.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 10A illustrates a reaction scheme to synthesize a diol functional sulfobetaine (SB).

FIG. 10B illustrates an embodiment of a synthetic scheme for synthesis of sulfobetaine (SB) containing polyurethane ureas hereof.

FIG. 17A illustrates a small diameter conduit formed via electrospinning of a PCSUU 25/75 polymer.

FIG. 17B illustrates a portion of the conduit of FIG. 15B at greater magnification.

FIG. 18A illustrates photomicrographs of studies of ovine platelet deposition on an electrospun sheet of a PCSUU 100/0 polymer at two different magnifications.

FIG. 18B illustrates photomicrographs of studies of ovine platelet deposition on an electrospun sheet of a PCSUU 25/75 polymer at two different magnifications.

FIG. 23A illustrates a SEM photomicrograph image of albumin-FITC loaded PSBEU-COOH particles.

FIG. 23B illustrates a confocal microscopy image of albumin-FITC loaded PSBEU-COOH particles.

FIG. 24 illustrates a schematic illustration of a microparticle of PSBEU-COOH loaded with a drug such as paclitaxel, protein or enzyme (represented as crosshatched circles).

DETAILED DESCRIPTION

Figure 1B:
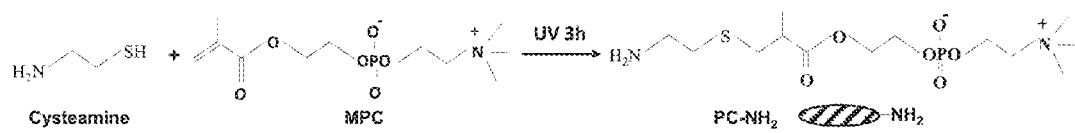
FIG. 1B illustrates an embodiment of a reaction scheme for synthesis of amine functional-phosphorylcholine (PC-NH$_2$) used in the reaction scheme of FIG. 1A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a zwitterion" includes a plurality of such zwitterions and equivalents thereof known to those skilled in the art, and so forth, and reference to "the zwitterion" is a reference to one or more such zwitterions and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

In a number of embodiments hereof, biodegradable, anti-thrombogenic or nonthrombogenic polymers are provided which are, for example, suitable for controlled release of one or more compounds such as drugs. Such polymers may, for example, be used in clinical applications such as drug eluting stent coatings or as vascular engineering temporary scaffolds. The polymeric materials are also biodegradable. The biodegradable polymer hereof may, for example, include groups having anti-thrombogenic properties along the length of the polymer and biodegradable groups in the backbone of the polymer. The anti-thrombogenic groups may, for example, be zwitterions or zwitterionic. A zwitterion is a neutral molecule with one or more positive electrical charges and one or more negative electrical charges. Examples of such groups include, but are not limited to, phosphorylcholine groups (a phosphobetaine-type zwitterionic group), sulfobetaine groups, carboxybetaine groups and derivatives of such groups.

In a number of embodiments, the polymers hereof are biodegradable soft segment polymers. The soft segments of the polymers hereof may, for example, include biodegradable groups such hydrolytically unstable groups. Biodegradable group may, for example, include esters, orthoesters, thioether-esters, anhydrides, amides, carbonates and/or peptides.

The term "polymer" refers generally to a molecule of high relative molecular mass/weight, the structure of which includes repeat units derived, actually or conceptually, from molecules of low relative molecular mass (monomers). The term "oligomer" refers generally to a molecule of intermediate relative molecular mass, the structure of which includes a small plurality of units derived, actually or conceptually, from molecules of lower relative molecular mass (monomers). In general, a polymer is a compound having >1, and more typically >10 repeat units or monomer units, while an oligomer is a compound having >1 and <20, and more typically leas than ten repeat units or monomer units. In a number of embodiment, biodegradable polymers hereof degrade into biocompatible degradation products.

In a number of embodiments, the polymers hereof are polyurethanes. In a number of embodiments, a multi-functional isocyanate component (typically having an average isocyanate functionality of two or more) used in forming the polyurethanes hereof includes multi-functional isocyanates or multi-isocyanates (that is, having, two or more isocyanate groups). In a number of embodiments, the multi-functional isocyanates or multi-isocyanates are aliphatic multi-isocyanates. Specific examples include diisocyanatobutane, hexamethylene di-isocyanate, lysine di-isocyanate ("LDI") and derivatives thereof (e.g., alkyl esters such as methyl or ethyl esters) and lysine tri-isocyanate ("LTI") and derivatives thereof (e.g., alkyl esters such as methyl or ethyl esters). Dipeptide derivatives can also be used. For example, lysine can be combined in a dipeptide with another amino acid (e.g., valine or glycine). In addition, isocyanates prepared from putrescine (diamino butane) can be used as well. One class of suitable multi-isocyanates includes generally those multi-isocyanate derived from biocompatible multi-functional amines. As used herein, the term "biocompatible" refers generally to compatibility with living tissue or a living system.

In forming polyurethanes and/or polyurethane ureas, a multi-functional isocyanate component including the multi-functional isocyanates or multi-isocyanates may be reacted with a multi-functional active hydrogen component. The multi-functional active hydrogen component includes one or more multi-functional active hydrogen reactants. The multi-functional active hydrogen reactants typically have an average active hydrogen functionality of at least 2. The term "average" reflects the fact that the multi-functional reactants can include multiple types of multi-functional reactants. Suitable multi-functional active hydrogen reactants include, for example, polyols (that is, having more than on hydroxyl functionality), polyamines (that is, having more than one amine functionality), and polythiols (that is, having more than one thiol functionality). Chain extenders for use in polyurethanes hereof may, for example, include diols, diamines and/or peptides.

The polymer hereof may, for example, be loaded with many types of biologically active agents or compounds, including, for example, drugs. Biologically active or bioactive agents may be synthetic molecules, biomolecules, or multimolecular entities and include, but are not limited to, proteins, enzymes, organic catalysts, ribozymes, organometallics, glycoproteins (for example, proteoglycan), glycosaminoglycans (for example, hyaluronic acid or HA), peptides, polyamines, polyamino acids, antibodies, nucleic acids, cytokines, carbohydrates, oleophobics, lipids, components of extracellular matrix, growth factors, hemostatic agents, pharmaceuticals, chemotherapeutics, and therapeutics.

The biologically active compound may, for example, include or be a drug or pharmaceutical such as an amphetamine, a steroid, an anesthetic, an analgesic, an antacid, an antibiotic, an anticoagulant, an antidepressant, an antidote, an antihistamine, an anti-inflammatory, an antimycotic, an anti-proliferative agent, an anticancer agent, an analgesic agent, an antirejection agent, an antiretroviral, an antiviral, a barbiturate, a beta blocker, a booster, a contraceptive, a decongestant, a depressant, an emetic, an expectorant, a hypnotic, an immunosuppressant, a laxative, a narcotic, a neurochemical, an opiates, a painkiller, a prophylactic, a purgative, a relaxant, a sedative, a statin, a suppressant, a tranquilizer, a vaccine, a vitamin or a prodrug thereof. In a number of embodiments, the biologically active agent is an anti-proliferative agent, an antibiotic, an antiviral, an antimycotic, an anticancer agent, an immunosuppressant, a chemotherapeutic agent, an anti-rejection agent, an analgesic agent, and/or an anti-inflammatory agent.

In a number of embodiments, the polymeric materials are biodegradable, elastomeric and thermoplastic polyurethanes that contain anti-thrombogenic non-thrombogenic groups (for example, along the backbone of the polymer). Anti-thrombogenic groups such as phosphorylcholine (PC), sulfobetaine (SB) or carboxybetaine may, for example, be integrated into the biodegradable polyurethanes by pendant grafting and/or backbone conjugation. Anti-thrombogenic groups improve surface hemocompatibility and may, for example, provide resistance against protein adsorption and/or platelet adhesion. Such groups may, for example, achieve low biointeractions and reduce inflammatory host responses for various biomedical and biotechnological applications.

The degradable characteristics of the polymeric materials hereof arise from the incorporation of biodegradable group such as hydrolytically labile bonds (for example, esters) along the backbone of the polymer. When loaded with, for example, an anti-proliferative drug such as paclitaxel and coated onto the surface of, for example, vascular stents, the materials hereof have the capacity to deliver the drug over a period of time (for example, several weeks). Furthermore, in a number of embodiments, high elasticity of the materials hereof enables the materials to undergo high levels of distension without fracture. Such high elasticity is, for example, compatible with the coating of materials that need to be expanded when placed in situ.

In a number of embodiments, the materials hereof are thermoplastic elastomers. Such materials are readily applied in solvent-based coating approaches and also are easily loaded with pharmaceutical agents. For tissue engineering applications in, for example, the cardiovascular system, maintaining non-thrombogenic character throughout the period prior to complete degradation is desirable. The polymer systems hereof exhibit such characteristics.

In a number of representative studies, the polymeric materials hereof were applied to stents to, for example, address the problem of late stent thrombosis. In such studies, a biodegradable anti-thrombogenic polymer with anti-proliferative drug release as a stent coating was developed with an objective of reducing thrombogenicity while concurrently limiting restenosis. A material exhibiting biodegradability, elasticity (mechanical matching), non-thrombogenicity (anti-thrombosis) and drug loading capacity (for example, for intimal hyperplasia inhibition) is desirable, for example, as a drug eluting coating for vascular stents and as matrix materials for vascular grafts. Non-thrombogenic groups (for example, phosphorylcholine (PC) or sulfobetaine (SB)) were integrated into the biodegradable polyurethanes by pendant grafting and/or backbone conjugation.

In a number of the representative studies, biodegradable elastomeric poly(ester urethane)ureas (PEUUs) with 2-methacryloyloxyethyl phosphorylcholine or with sulfobetaine were synthesized to improve the hemocompatibility. Surface hydrophilicity, thermal properties, mechanical properties, degradation properties, and blood contact response were characterized. The blood compatibility was evaluated by ovine blood contact. Furthermore, anti-proliferative drug paclitaxel was loaded into the polymer to evaluate the release kinetics/profile and released drug bioactivity. The polymers hereof were, for example, coated on a magnesium alloy coil stent by dip-coating to evaluate surface blood contact response. The polymers were also electrospun into small diameter conduits.

The biodegradable, elastomeric polymers with anti-thrombogenic moieties hereof significantly decrease blood platelet deposition. The polymers are suitable to load one or more bioactive agents such as an anti-proliferative drug (for example, paclitaxel) and to release the drug for a period of time after burst release in 10% ethanol/PBS solution. Paclitaxel-loaded polyurethane films hereof showed inhibition of vascular smooth muscle cell proliferation. The polymers hereof could readily be coated on, for example, vascular coil stents and electrospun into a small diameter conduit. The coated stent prototype exhibited reduced platelet deposition in vitro. As described above, the non-thrombogenic elastomers hereof may, for example, serve as a drug eluting coatings for a metallic vascular stent or other implantable devices and as a scaffold for vascular and/or other tissue engineering applications. In general, the polymers hereof are suitable for use in connection with any type of blood contacting or other article (for example, as a coating).

The antithrombogenic groups of the polymers hereof are integral throughout the polymer. In a number of studies, poly(ester urethane) urea containing functional groups reactive with a functional group on an antithrombogenic agent was first synthesized. For example, poly(ester urethane) urea containing carboxyl groups (PEUU-COOH) was synthesized from multi-functional active hydrogen component including a soft segment of a polyester including multiple active hydrogen functional groups and a compound including at least one carboxyl group and multiple active hydrogen functional groups, and a multi-isocyanate component. Reactants including a single active hydrogen function group or a single isocyanate group can be used in a reaction mixture hereof, but will result in termination of chain growth. In several embodiments, a polycaprolactone (PCL) diol, dimethylolpropionic acid (DMPA), a hard segment diisocyanatobutane, and a chain extender putrescine were reacted to form PEUU-COOH as illustrated in FIG. 1A.

Figure 1A:
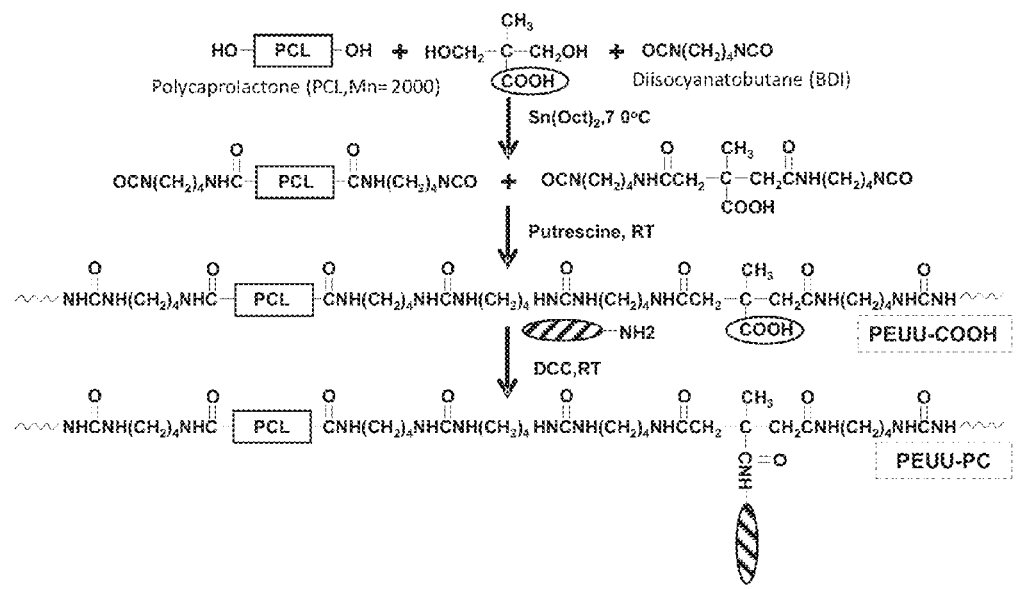
FIG. 1A illustrates an embodiment of a reaction scheme for synthesis of a zwitterion-containing poly(ester urethane) ureas hereof.

Aminated phosphorylcholine was synthesized as illustrated in FIG. 1B and then grafted onto the PEUU-COOH by a condensation reaction to achieve the final product, PC containing PEUU or PEUU-PC (see FIG. 1A). The chemical structure, surface atomic composition, surface hydrophilicity, mechanical properties, and degradation of the polyurethanes were characterized. Ovine blood contact testing was performed to assess acute blood compatibility. Finally, the conventional antiproliferative drug, paclitaxel, was loaded into polyurethane films and the release profile and antiproliferative bioactivity of released drug was evaluated in vitro.

The synthesis of PEUU-PC was confirmed by 1H NMR, and XPS confirmed the surface presence of the PC moieties (Table 1). The introduction of carboxylic groups in PEUU-COOH was verified by a weak and broad peak at $\delta=12.24$ ppm, while this peak was not found in either PEUU or PEUUPC. A specific chemical shift at 3.14 ppm was assigned to —N(CH$_3$)$_3$ of phosphorylcholine in PEUU-PC, while the chemical shift was not observed on the 1H NMR spectra of PEUU and PEUU-COOH. Other specific peaks were assigned to methylene groups. In Table 1, the rise in surface oxygen for the PEUU-COOH surface compared with PEUU was consistent with the presence of a carboxyl group, while the increase in surface nitrogen as well as the detection of phosphorus on the PEUU-PC surface was interpreted to indicate PC grafting onto PEUU-COOH. Polymer surface hydrophilicity as reflected in water contact angle measurements in air (Table 2) showed increased hydrophilicity with PEUU-COOH. The DSC spectra of the polymers showed glass transition temperatures (Tgs) lower than −50° C. (Table 2) and melt temperatures (Tms) attributable to the PCL segments ranging from 34 to 40° C. All polymers were in a rubbery state at room temperature as a result of their low Tgs (<−50° C.), which is physically compatible with a coating application to expandable vascular stents. There was a decrease in tensile strength for PEUU-COOH and PEUU-PC relative to PEUU (Table 2), while PEUU-PC showed a significantly higher breaking strain than PEUU and PEUU-COOH.

TABLE 1[a]

| samples | C | O | N | P |
|---|---|---|---|---|
| PEUU | 73.4 ± 3.3 | 21.7 ± 0.7 | 2.0 ± 0.3 | 0.0 ± 0.0 |
| PEUU-COOH | 71.5 ± 4.1 | 21.9 ± 3.8 | 21.9 ± 3.8 | 0.0 ± 0.0 |
| PEUU-PC | 67.1 ± 3.2 | 18.4 ± 4.1 | 4.4 ± 1.4 | 0.2 ± 0.1 |

[a]Atomic percentage determined by X-ray photoelectron spectroscopy (XPS).

TABLE 2[a]

| Samples | tensile strength (MPa) | strain (%) | water contact angle (°) | Tg (° C.) | Tm (° C.) |
|---|---|---|---|---|---|
| PEUU | 34 ± 3[a] | 660 ± 85[a] | 80 ± 2[a] | −52 | 40 |
| PEUU-COOH | 22 ± 2[b] | 649 ± 77[a] | 70 ± 2[b] | −58 | 34 |
| PEUU-PC | 22 ± 5[b] | 1250 ± 221[b] | 53 ± 2[c] | −51 | 36 |

[a], b, and c denote statistically distinct groups for each measured

As described above, the hydrophilicity of poly(ester urethane)ureas was significantly increased after carboxyl group introduction, and was highest after PC moiety grafting. Compared with carboxyl groups, PC groups exposed on polymer film surfaces would have higher hydrophilicity, to putatively reduce protein adsorption. Also, with this increase in polymer hydrophilicity, these polymers could be expected to undergo accelerated hydrolytic degradation.

Figure 2:
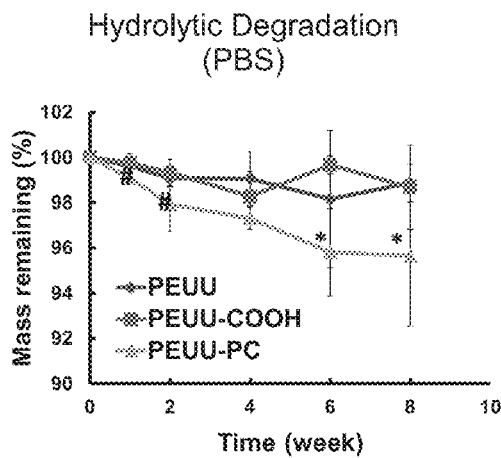
FIG. 2 illustrates a study of in vitro hydrolytic degradation of a poly(ester urethane) urea (PEUU), a carboxyl functional poly(ester urethane) urea (PEUU-COOH) and a phosphorylcholine functional poly(ester urethane) urea (PEUU-PC) as illustrated in FIG. 1.
Figure 3:
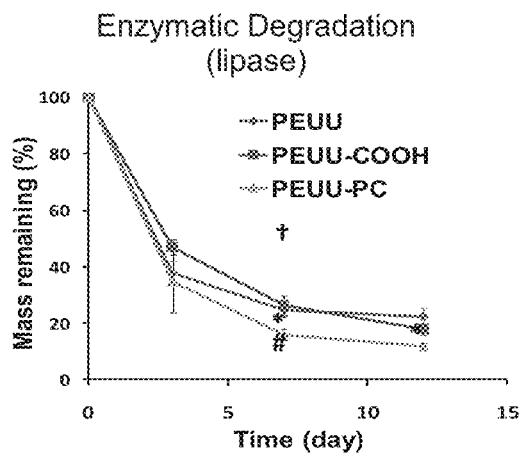
FIG. 3 illustrates a study of in vitro enzymatic (lipase) degradation of PEUU, PEUU-COOH and a PEUU-PC.

Degradation studies showed faster degradation for PEUU-PC relative to PEUU and PEUU-COOH over 8 wks in aqueous or enzymatic environments. In that regard, polymer degradation was evaluated in both PBS and PBS with lipase at 37° C. (FIGS. 2 and 3, respectively). For hydrolytic degradation in PBS (FIG. 2), PEUU and PEUU-COOH showed statistically equivalent behavior without significant mass loss at 8 wks (p>0.05), while PEUU-PC did show mass loss over this period. In lipase solution (FIG. 3), all polymers showed markedly faster degradation than in PBS solution. Within 12 days, PEUU-PC showed more mass loss than either PEUU and PEUU-COOH, which exhibited the very similar degradation behavior. This result was similar to the trends in degradation behavior observed in PBS.

The hydrolytic enzyme lipase may be used to accelerate the degradation of polymers containing, for example, ester, carbonate, urethane, urea, and amide groups. The use of enzyme-containing buffers, therefore, allows the investigation of slower degrading polymers in an accelerated time frame. It is possible to control the degradation behavior in the polymers hereof. For example, introducing more hydrophilicity into the polymer backbone with, for example, PEG segments acts to speed degradation. Moreover, switching esters to, for example, carbonates generally slows degradation. For specific enzymatic sensitivity, it is possible to introduce peptide sequences into the backbone that are responsive to a particular enzyme.

Figure 4A:
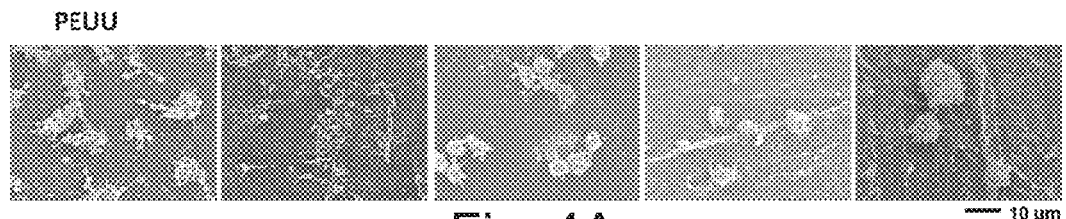
FIG. 4A illustrates photomicrographs of bovine platelet deposition on PEUU.
Figure 4B:
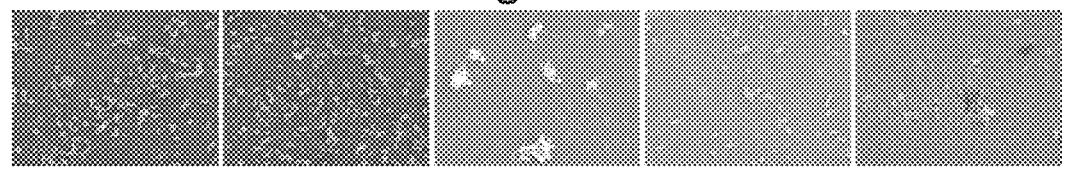
FIG. 4B illustrates photomicrographs of bovine platelet deposition on PEUU-COOH.
Figure 4C:
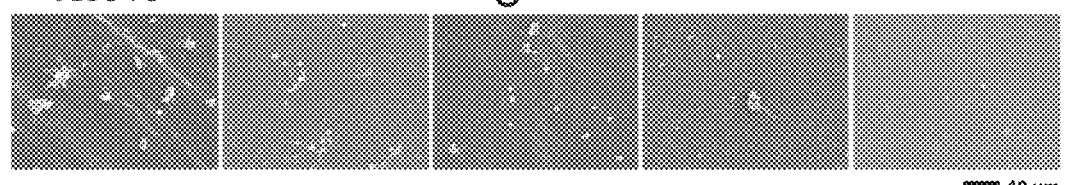
FIG. 4C illustrates photomicrographs of bovine platelet deposition on PEUU-PC.
Figure 5:
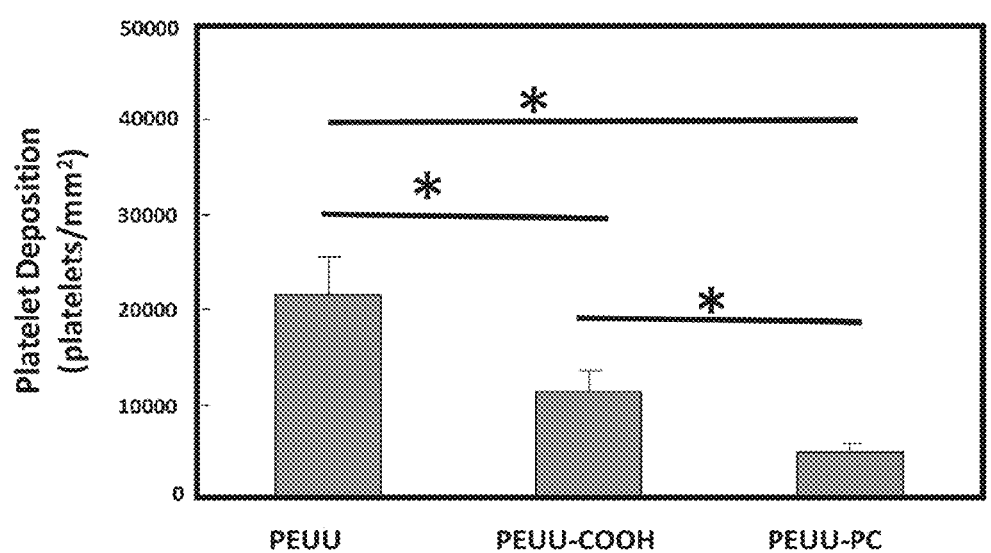
FIG. 5 illustrates a graph of platelet deposition (platelets/mm$^2$) for PEUU, PEUU-COOH and PEUU-PC.

Nonthrombogenicity and the prevention of intimal hyperplasia are two important features desired in polymer-coated, drug-eluting, vascular stents. Scanning electron micrographs of polymer film surfaces following ovine blood contact qualitatively demonstrated reduced ovine platelet deposition on polyurethanes with carboxyl groups and further reductions in the presence of PC groups (FIG. 4). After 2 h of blood contact, a large number of platelet aggregates were observed on PEUU surfaces with pseudopodia extensions (FIG. 4A). On PEUU-COOH surfaces, many individual deposited platelets were visible, with significantly fewer aggregates and pseudopodia extension present, but at a lower level (FIG. 4B). For PEUU-PC, only sparse deposition was observed of individual platelets, with some of these platelets displaying pseudopodia extension (FIG. 4C). Platelet deposition quantified using the LDH assay (FIG. 5) confirmed the visual results, with PEUU-PC exhibiting significantly lower platelet deposition than PEUU-COOH and PEUU.

PC group grafting was thus associated with reduced acute ovine blood platelet deposition in vitro. PC (and/or other zwitterion) containing polymers hereof may, for example, exhibit a reduced cellular affinity resulting from high free water fraction on the surface as a result of the zwitterionic nature of PC, resistance to protein adsorption, limited plasma protein activation, and lateral mobility of molecules. In addition to nonthrombogenicity, PC-containing polymers hereof may also result in reduced inflammatory response and negligible cytotoxicity. As a secondary effect to its inhibition of cell adhesion, the PEUU-PC may be expected to have a negative effect on intimal hyperplasia, even without the controlled release of an antiproliferative agent.

Figure 6:
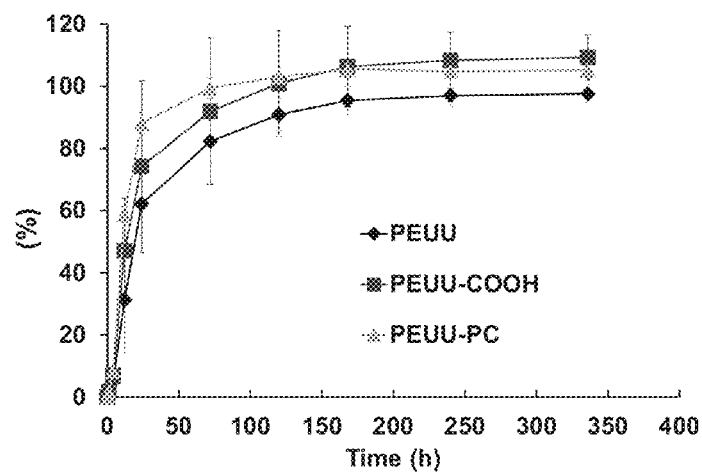
FIG. 6 illustrates the release of paclitaxel from films of PEUU, PEUU-COOH and PEUU-PC in 10% ethanol/PBS solution at 37° C.

A 60-85% burst release of paclitaxel took place in a 10% ethanol/PBS solution at 37° C. for each of PEUU, PEUU-COOH and PEUU-PC polymer films within 24 h as illustrated FIG. 6. The release profiles then exhibited a slower release for 5 days. For the entire release measurement period, the paclitaxel (TAXOL® available from Bristol-Myers Squibb Company of New York, N.Y.) release rates of PEUU-COOH and PEUU-PC were significantly higher than for PEUU, while no significant difference was observed between PEUU-COOH and PEUU-PC. Without limitation to any mechanism, PEUU-COOH and PEUU-PC may, for example, show significantly greater release over the study period as a result of their higher hydrophilicity.

Because paclitaxel is a highly hydrophobic small molecule, ethanol was mixed into the PBS collection fluid to improve paclitaxel solubility and accelerate its release. Thus, actual paclitaxel release times in an aqueous physiological system may be much longer than 5 days. Furthermore, the burst release observed was attributed to the low Tgs (<−50° C.) of the polyurethanes, which resulted from the PCL of the soft segment. The paclitaxel release kinetics for the polyurethanes were similar to that for neat PCL.

Figure 7:
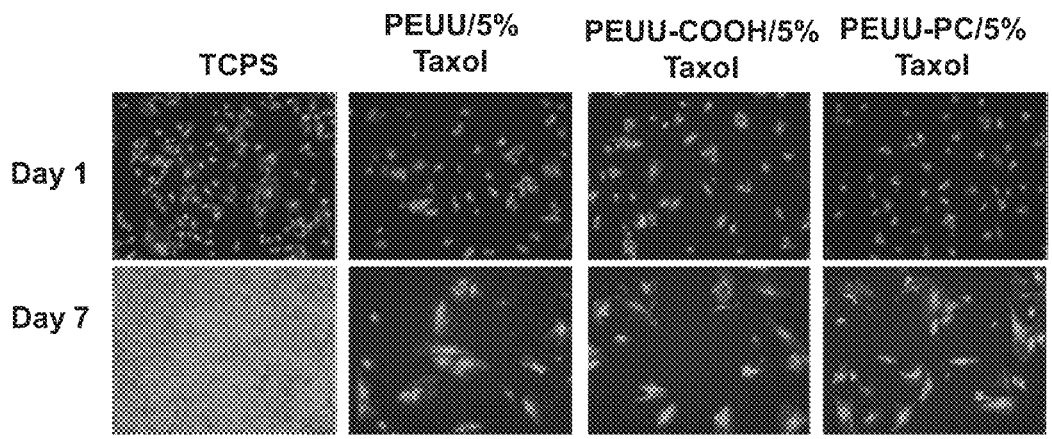
FIG. 7 illustrates photomicrographs in a study of bioactivity of released paclitaxel (rat smooth muscle cells (rSMC) growth inhibition) after 1 day and after 7 days on tissue culture polystyrene (TCPS), PEUU, PEUU-COOH and PEUU-PC.
Figure 8:
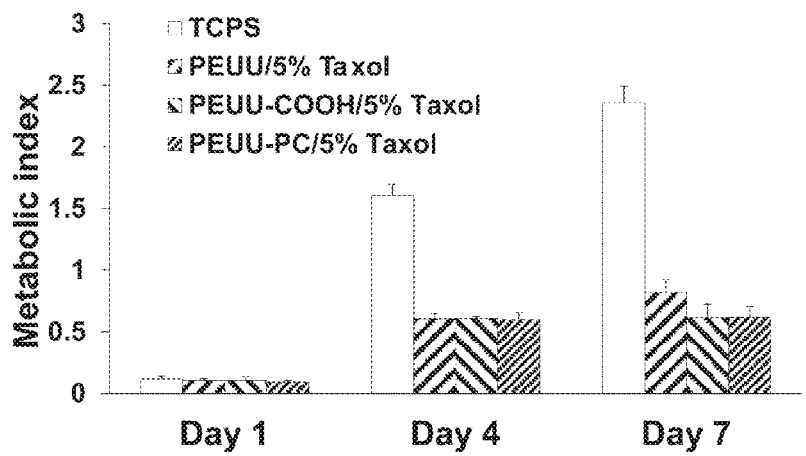
FIG. 8 illustrates metabolic index a day 1, day 4 and day 7 for TCPS, PEUU, PEUU-COOH and PEUU-PC.

The bioactivity of released paclitaxel from the polymer films was evaluated by placing drug-loaded films into cell culture wells pre-seeded with rSMC. In FIG. 7, without paclitaxel treatment, rSMCs on TCPS showed obvious cellular proliferation and had reached confluence by day 7. However, when any of the three polymers containing paclitaxel were present in the TCPS culture wells, rSMC numbers did not appear to increase under fluorescence microscopy. Live/dead cell staining indicated no apparent cellular death in any of the wells with paclitaxel-releasing polymer. Day 7 micrographs in the presence of paclitaxel were similar to those observed at day 4 (data not shown in FIG. 7). Furthermore, metabolic measurements of rSMCs without paclitaxel release showed an increase in this parameter at 4 and 7 days, in significant contrast to those wells with rSMCs with paclitaxel-releasing polymers (FIG. 8) where metabolic index values increased at day 4 but did not increase further at day 7. The rSMC inhibition results thus confirmed paclitaxel maintained its bioactivity after polymer loading and solvent contact, indicating, for example, suitability for application in solvent-based device coating. Alternative antiproliferative drugs, such as everolimus, zotarolimus, and sirolimus may also or alternatively be used. The rSMC size at day 7 with paclitaxel treatment appeared to be greater than that at day 1. This effect may, for example, attributed to rSMC spreading at later time points, particularly with paclitaxel treatment providing relatively more available surface area due to inhibited proliferation.

The biodegradable PEUU-COOH, which was an intermediate product or precursor polymer and control material in this study, and other functional biodegradable polymers hereof have the potential to be applied to a variety of biomedical material applications. The data showed PC grafting further reduced platelet deposition relative to the carboxylic-enriched surface of PEUU-COOH, although the latter was also associated with reduced thrombogenicity compared to PEUU. Moreover, the active carboxyl groups (and/or other functional groups) in the polymers hereof could be conjugated with bioactive molecules containing amino or hydroxyl groups, including peptides, growth factors, drugs, and even fluorescent agents. Physical bonding with such molecules might also be achieved. Moreover, by reacting only a portion of the functional groups of the biodegradable polymer such as PEUU-COOH with a zwitterion containing compound, polymer with both zwitterion functionality and other functional groups (for example, carboxyl groups) can be formed. As described further below, such functional groups may, for example, be used to covalently tether the biodegradable polymers hereof to a surface.

Also synthesized in this study was a functionalized phosphorylcholine (PC) molecule containing a 1:1 PC/amino group ratio. The synthesis utilized a photoinitiator (benzophenone), although photoinitiation might not be necessary for this reaction. With photoinitiator use, one could also prepare amino-functional macromolecules (or polymers), which have repeating PC moieties, and the chain length of PC macromers could be controlled by manipulating the initial monomer feed ratio via a thiol-ene radical photopolymerization reaction.

Figure 9A:
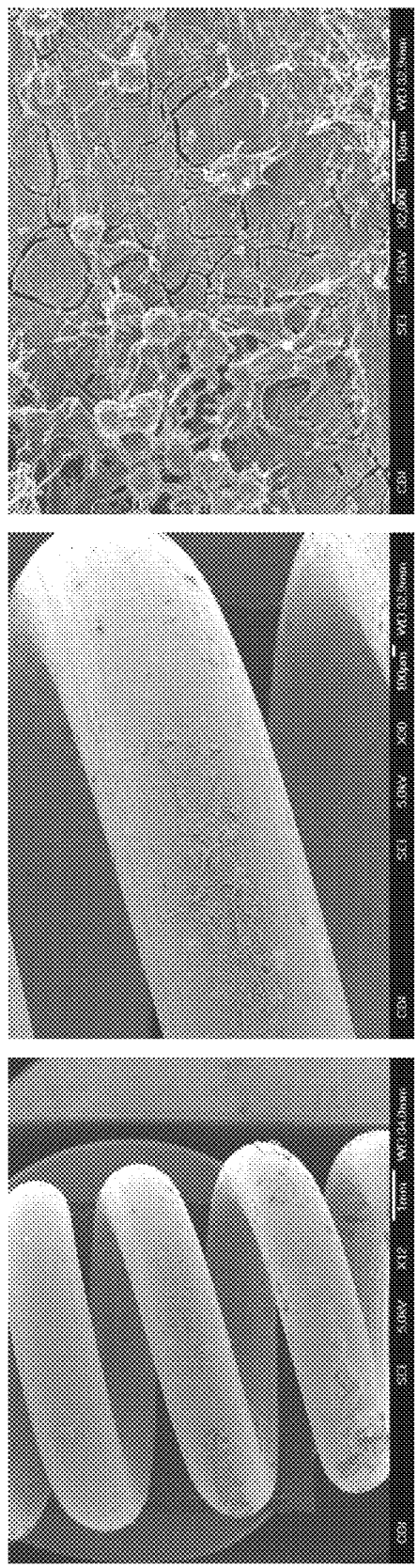
FIG. 9A illustrates ovine platelet deposition (2 hours) on an uncoated magnesium AZ31 stent at three different magnifications.
Figure 9B:
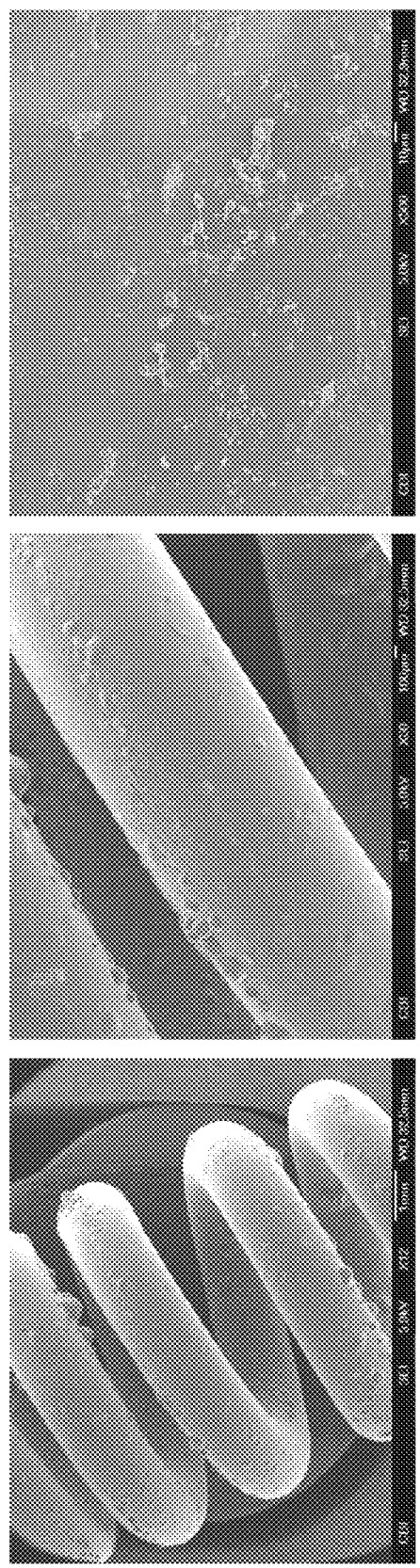
FIG. 9B illustrates ovine platelet deposition (2 hours) on a PEUU-PC coated magnesium AZ31 stent at three different magnifications.

FIG. 9A illustrates ovine platelet deposition (after 2 hours) on an uncoated magnesium AZ31 stent at three different magnifications. FIG. 9B illustrates ovine platelet deposition (after 2 hours) on a PEUU-PC coated magnesium AZ31 stent at three different magnifications. The stents were cleaned using trichloroethylene and UV plasma before dip-coating. As in the above studies, the PEUU-PC coated stent exhibited limited platelet deposition.

The amount of PC in PEUU-PC in the studied polymers hereof may be limited by the number of free carboxyl groups in the PEUU-COOH. Such a limit may follow from a side reaction between the carboxyl group and diisocyanate in dimethylolpropionic acid (DMPA), although diisocyanate is primarily reacted with the two hydroxyl groups in DMPA. When DMPA reached 50 molar % in the soft segments, the achievable molecular of the polyurethanes was limited. Reactive functional groups other than carboxyl groups can be used to attached zwitterionic compounds to biodegradable polymers hereof. For example, PEUU with variable amount of amino groups (PEUU-NH$_2$) also has been synthesized by using N-Boc-Seriol (as a substitute of the DMPA) and modified with a zwitterionic compound including functional groups reactive with amino groups. In the above examples, a biodegradable poly(ester urethane) urea was introduced by grafting aminated phosphorylcholine onto carboxyl groups containing biodegradable poly(ester urethane) urea. Anti-thrombogenic entities can also be introduced into the backbone of a polyurethane polymer via, for example, the reaction of a reactant including one or more anti-thrombogenic compounds (for example, zwitterions) and one or more (typically more than one) hydrogen reactive functionalities as described above (wherein the anti-thrombogenic compounds maintain their anti-thrombogenic characteristics after reaction). For example, FIG. 10A illustrates a reaction scheme to synthesize a diol functional sulfobetaine (SB). FIG. 10B illustrates a reaction scheme in which polycaprolactone (PCL) diol, the SB-diol and diisocyanatobutane are reacted at PCL/SB molar ratio of 100/0, 75/25, 50/50, 25/75 or 0/100. After that reaction, the chain extender putrescine was added to form polyurethane urea polymer include PCL and SB in the backbone thereof (PCSUU).

Figure 11:
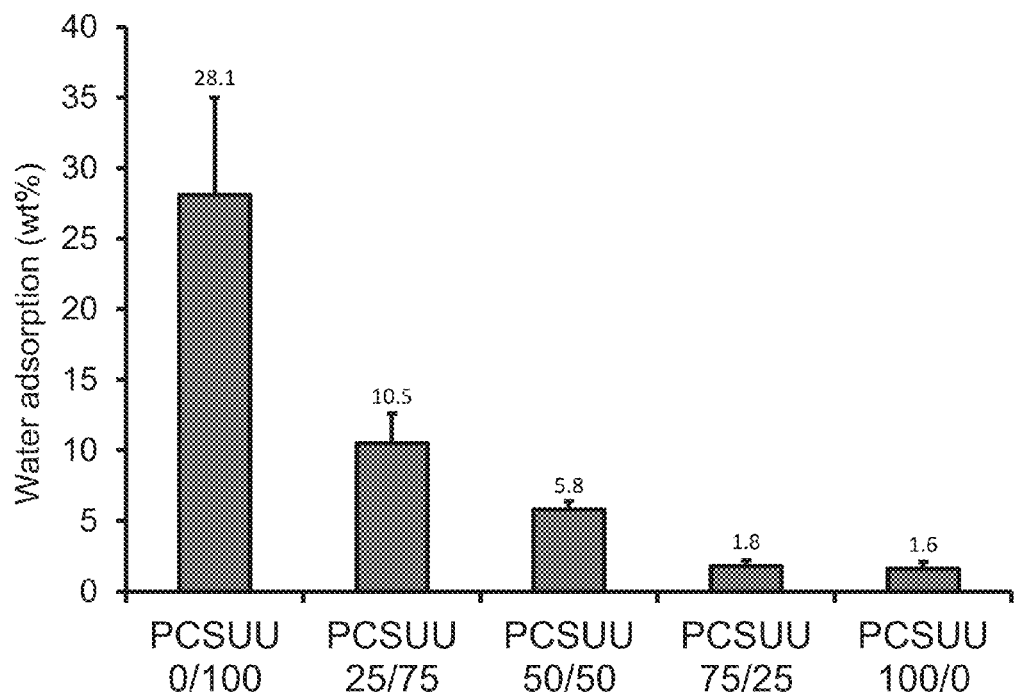
FIG. 11 illustrates stress-strain curves for films of SB containing polyurethane ureas (PCSUU) synthesized as illustrated in FIG. 10 at various molar ratios of polycaprolactone (PCL) to SB.

The PCSUU chemical structure was confirmed by coexistence of chemical shifts at 1.0, 2.1, 3.55 and 4.4 ppm assigned to SB and at 2.35 and 4.06 ppm assigned to PCL. FTIR spectra peaks at 1035 cm$^{-1}$ (—SO3) further proved successful synthesis. Glass transition temperatures of PCSUUs containing PCL were lower than −50° C. However PCSUU 0/100 had two Tgs of 14 and 111° C. PCSUU 100/0 had a melt temperature (Tm) at 32° C., and no Tm appeared for PCSUU 0/100. Water absorption studies indicated PCSUU hydrophilicity increased with SB content. PCSUU 0/100 had the highest water uptake at 28%, while PCSUU 75/25 and PCSUU 100/10 had 2%, and PCSUU 75/25 and 50/50 were 11% and 6%, respectively (see FIG. 11).

TABLE 3

| Sample | Tensile strength (MPa) | Strain at breaking (%) | Initial modulus (MPa) |
| --- | --- | --- | --- |
| PCSUU 100/0 | 31 ± 2 | 998 ± 115 | 29 ± 4 |
| PCSUU75/25 | 45 ± 5 | 962 ± 121 | 38 ± 9 |
| PCSUU 50/50 | 45 ± 4 | 1197 ± 102 | 28 ± 7 |
| PCSUU 25/75 | 38 ± 3 | 849 ± 68 | 62 ± 26 |
| PCSUU 0/100 | 21 ± 5 | 130 ± 35 | 170 ± 75 |

Figure 12:
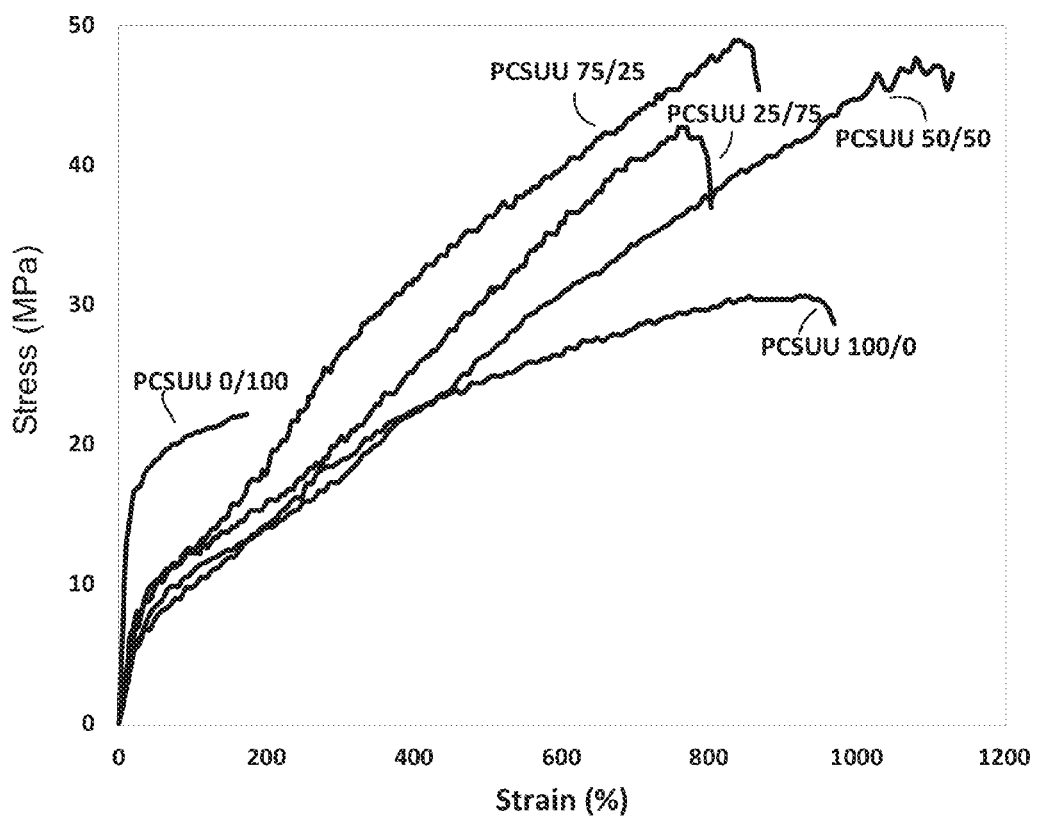
FIG. 12 illustrates water adsorption studies for films of SB containing polyurethane ureas (PCSUU) synthesized as illustrated in FIG. 10 for various molar ratios PCL to SB.

As set forth in Table 3, PCSUU 0/100 was relatively stiff with the lowest tensile strength (21±5 MPa) and strain (130±5%) as well as highest initial modulus (170±75 MPa), while PCSUUs containing PCL had tensile strengths of 31 to 45 MPa, strains of 849 to 1197% and initial moduli of 28 to 62 MPa. Stress strain study data are set forth in FIG. 12.

Figure 13:
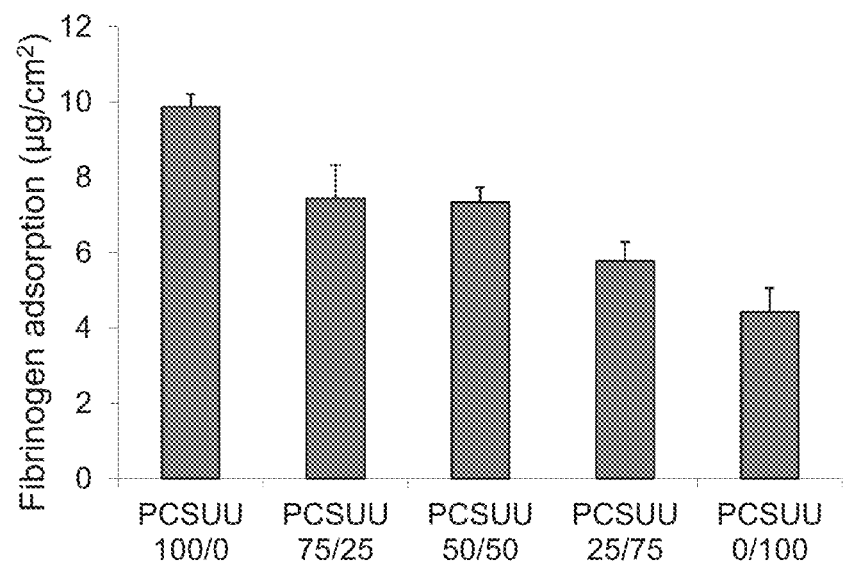
FIG. 13 illustrates protein (fibrinogen) adsorption studies on films of SB containing polyurethane ureas (PCSUU) synthesized as illustrated in FIG. 10 for various molar ratios of PCL to SB.
Figure 14:
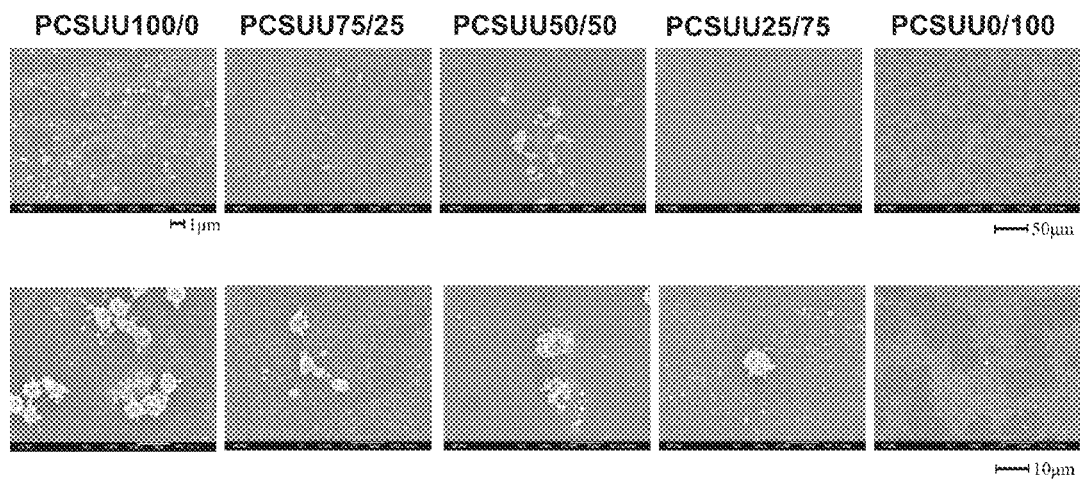
FIG. 14 illustrates photomicrographs of studies of ovine platelet deposition on films of SB containing polyurethane ureas (PCSUU) synthesized as illustrated in FIG. 10 for various molar ratios of PCL to SB.
Figure 15:
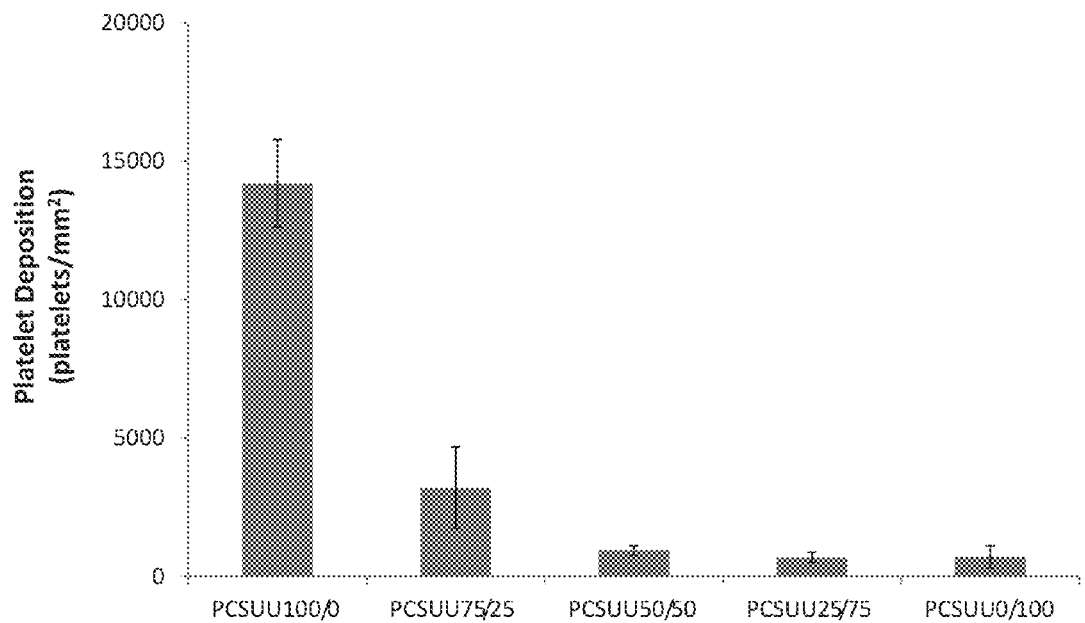
FIG. 15 illustrates a study of platelet deposition onto PCSUU films having various molar ratios of PCL to SB after contact with ovine blood as determined by a lactate dehydrogenase (LDH) assay.
Figure 16:
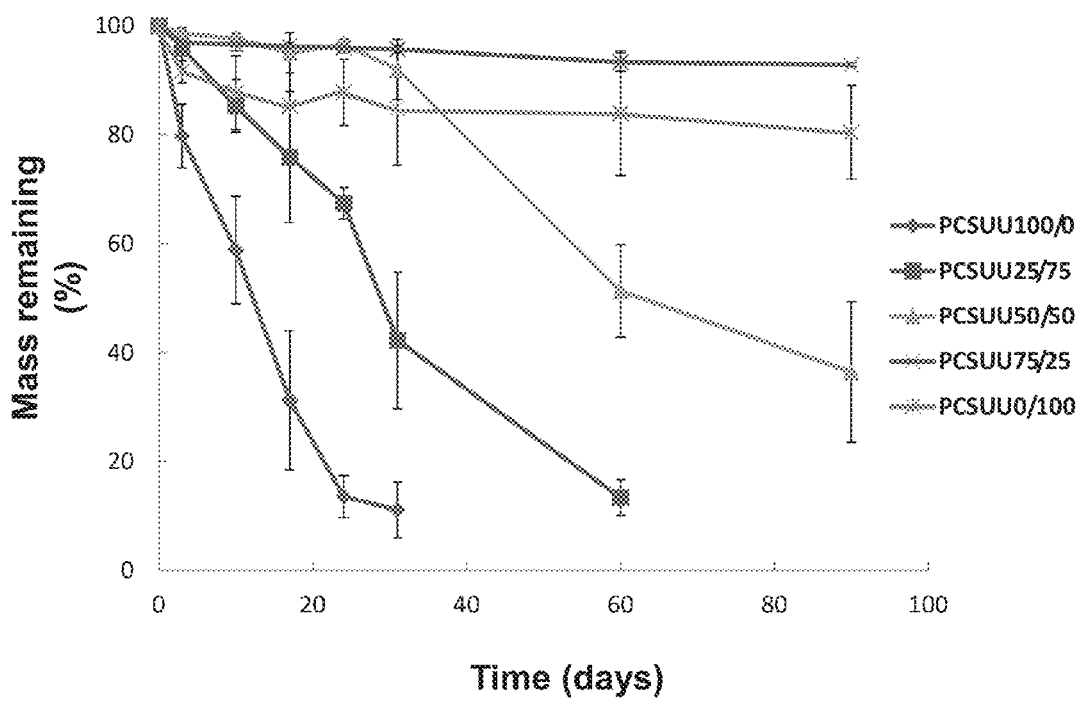
FIG. 16 illustrates degradation studies for PCSUU films having various molar ratios of PCL to SB.

As illustrated in FIG. 13, fibrinogen adsorption on PCSUU surfaces was reduced with increasing SB content and a similar trend was seen for platelet deposition (FIG. 14). FIG. 15 illustrates a study of platelet deposition onto PCSUU films having various molar ratios of PCL to SB after contact with ovine blood as determined by a lactate dehydrogenase (LDH) assay. FIG. 16 illustrates degradation studies for PCSUU films having various molar ratios of PCL to SB.

PCSUU 25/75 was electrospun into a 1.3 mm inner diameter conduit, forming continuous fibers without beading as illustrated in FIGS. 17A and 17B. FIG. 18A illustrates micrographs of ovine platelet deposition on an electrospun sheet of a PCSUU 100/0 polymer at two different magnifications. FIG. 18B illustrates micrographs of studies of ovine platelet deposition on an electrospun sheet of a PCSUU 25/75 polymer at two different magnifications. Once again, platelet deposition is found to decrease with increasing SB content.

The PCSUU polymers described above provide a family of elastomeric, biodegradable polyurethane ureas including variable soft segments of polycaprolactone and sulfobetaine diol, a diisocyanatobutane hard segment, and a putrescine chain extension. The synthesized polymers exhibited improved blood compatibility as relative sulfobetaine content increased, with decreased elastomeric behaviour when PCL was eliminated. The attractive mechanical properties and processability of these PCSUU polymers provide for applications including, but not limited to, material coating and porous scaffold formation.

Another SB-bearing polyurethane (poly (sulfobetaine ester urethane), PSBEU) was synthesized from sulfobetaine-diol (SB-diol), poly(carprolactone)-diol (PCL-diol, Mw=570) with a molar ratio of 75/25, after adding diisocyanatobutane (BDI) (BDI:diols=1:1) and $Sn(Oct)_2$ as a catalyst. The reaction scheme is similar to the scheme set forth in FIG. 10B without the addition of putrescine. The biodegradable SB-bearing polymer PSBEU may, for example, improve surface coating stability and drug release functionality from the non-thrombogenic biodegradable coating on Mg alloy surfaces. Effectiveness of the PSBEU coating on Mg alloys was investigated and compared with the other elastomer coatings. Furthermore, drug loadable micro-particles were prepared from a carboxyl-functional PSBEU polymer to, for example, design a drug eluting non-thrombogenic biodegradable polymer coating. The PSBEU polymer exhibited sticky gel-like behavior in water (or PBS), and readily adhered to various surfaces.

A carboxylfunctional PSBEU (PSBEU-COOH) was synthesized from the SB-diol, PCL-diol (Mw=2000) and dimethylopropionic acid (DMPA) with a molar ratio of 75/15/10. The chemical structure of PSBEU's was confirmed by $^1$H NMR and FT-IR. Both of PSBEU and PSBEU-COOH in the $^1$H NMR chart showed some specific picks originated from SB (at $\delta$=1.1-1.2 ppm) and PCL (at $\delta$=2.4-2.5, 4.1-4.2 ppm) and the introduction of carboxyl groups in PSBEU-COOH was verified by a weak and broad peak at $\delta$=12.6 ppm. FT-IR spectra of the PSBEU's also showed a specific absorption pick at 1040 $cm^{-1}$ (—$SO_3$—) originated from SB moiety. The degradation speed of PSBEU in a lipase solution (100 U/mL) at 37° C. (around 60% mass loss in 1 month) was faster than the above-described PCSUU 50/50 and PCSUU 25/75 elastomer (1-2% mass loss in 1 month) which has a composition of SB in the structure thereof.

Figure 19A:
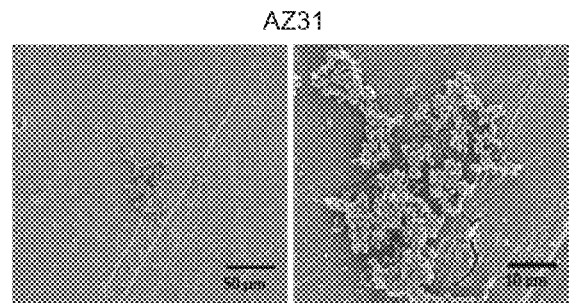
FIG. 19A illustrates a SEM photomicrograph of an unmodified or uncoated Mg alloy sample after contact with fresh ovine blood (heparin 3 U/mL) for 2 hours at 37° C.
Figure 19B:
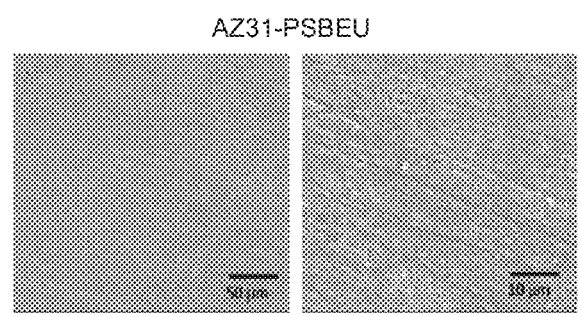
FIG. 19B illustrates a SEM photomicrograph of an Mg alloy sample coated with an SB-containing polyurethane (PSBEU) hereof after contact with fresh ovine blood (heparin 3 U/mL) for 2 hours at 37° C.
Figures 20A, 20B:
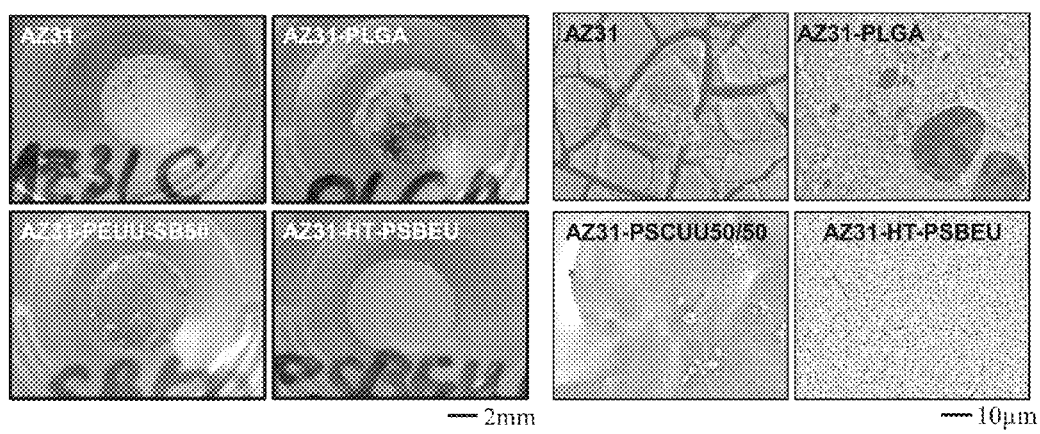
FIG. 20A illustrates macroscopic photographs of Mg alloys (AZ31) and poly(lactic-co-glycolic acid (PLGA 50/50), PCSUU 50/50 and PSBEU coated on Mg alloy surfaces after contact with citrated ovine blood for 4 hr at 37° C. (wherein "HT" designates hydrothermal pretreated).
FIG. 20B illustrates SEM photomicrographs of Mg alloys (AZ31) and PLGA 50/50, PCSUU 50/50 and PSBEU coated on Mg alloy surfaces after contact with citrated ovine blood for 4 hr at 37° C.
Figure 21:
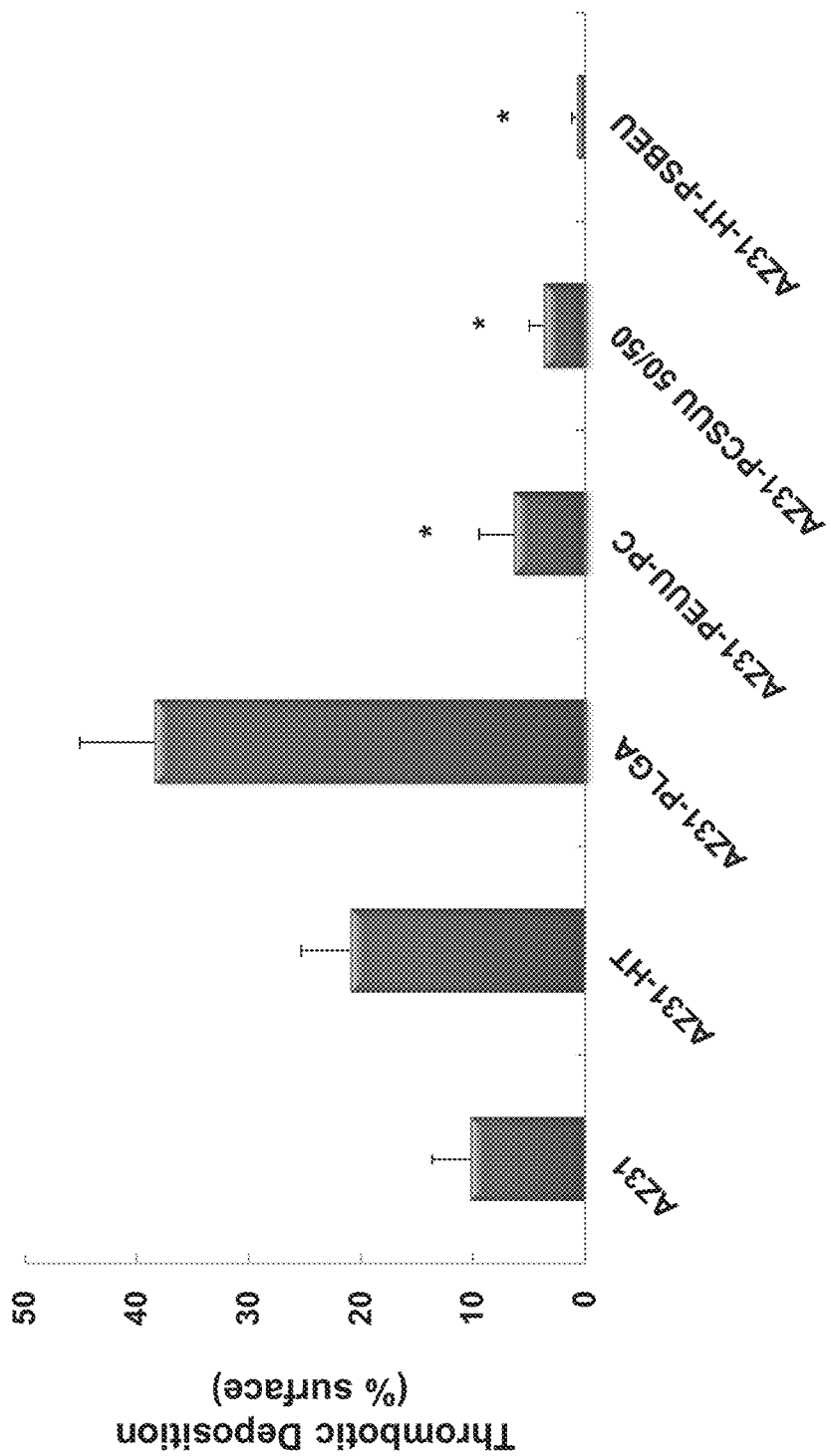
FIG. 21 illustrates surface coverage of biological adhesion on an uncoated AZ31 Mg alloy sample, an uncoated, heat treated (AZ31-HT) Mg alloy sample, as well as AZ31 and AZ31-HT Mg alloy samples coated with poly(lactic-co-glycolic acid (PLGA 50/50), PEUU-PC, PCSUU 50/50 and PSBEU after contact with fresh ovine blood for 4 hours as determined by Image-J analysis (*p<0.05 vs AZ31-HT & AZ31-PLGA, N=5).

To verify the coating effectiveness, Mg alloy test samples were dip coated in PSBEU solution dissolved in a solvent (2,2,2-trifluoroethanol or 1,1,1,6,6,6-Hexafluoroisopropanol), and the surface morphology was observed after the contact with fresh ovine blood under continuous rocking. Electron microscopy showed consistent deposition of platelets on unmodified AZ31 after blood contact with the deposited platelets in large aggregates and spread morphology (see FIG. 19A). In contrast, platelet deposition was sparse on the AZ31-PSBEU sample (FIG. 19B), and it was difficult to detect large platelet aggregates on the surfaces. Overall, surface deposition was significantly decreased on the modified surfaces versus the unmodified AZ31 control (p<0.05), and the deposition was similar or lower than found in previous studies with, for example, PCSUU as evaluated by Image-J software (see FIG. 21). FIG. 21 illustrates surface coverage of biological adhesion on an uncoated AZ31 Mg alloy sample, an uncoated, heat treated (AZ31-HT) Mg alloy sample, and AZ31 and AZ31-HT Mg alloy samples coated with poly(lactic-co-glycolic acid (PLGA 50/50), PEUU-PC, PCSUU 50/50 and PSBEU after contact with fresh ovine blood for 4 hours as determined by Image-J analysis. Platelet activation in the bulk phase quantified by flow cytometric measurement of Annexin V binding was significantly decreased in the blood contacted with AZ31-PSBEU (1.8±1.3%) compared to the AZ31 control (7.1±2.2%) (p<0.05, n=3). The surface corrosion performance and coating resistance were also investigated with immersion time in SBF at 37° C. for 8 days. Electrochemical impedance spectroscopy (EIS) was utilized to evaluate corrosion resistance of the modified Mg alloy samples. The initial coating resistances ($R_{coat}$) on AZ31-PSBEU (6.45× $10^6$ ohms) was significantly higher than for AZ31 control surfaces (3.71×$10^4$ ohms) However, the $R_{coat}$ on AZ31-PSBEU (6.37×$10^7$ ohms) was still elevated with respect to AZ31 control surfaces (1.42×$10^4$ ohms) at 8 days of immersion time point.

Figure 22A:
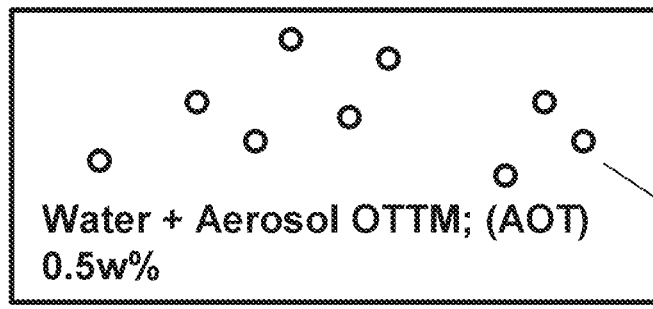
FIG. 22A illustrates preparation of a drug loadable and biodegradable and hemocompatible poly (sulfobetaine ester) urethane with carboxyl group functionality (PSBEU-COOH hereof.
Figure 22A:
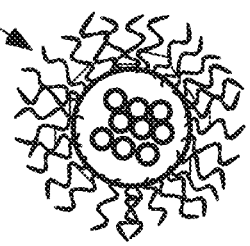

As described above, carboxylfunctional PSBEU-COOH was synthesized from the SB-diol, PCL-diol (Mw=2000) and DMPA with a molar ratio of 75/15/10. As illustrated in FIG. 22a, drug loadable micro-particles were prepared from the functional PSBEU-COOH polymer dissolved in dimethylsulfoxide (DMSO) dropped into deionized water with a surfactant (for example, dioctyl sodium sulfosuccinate (Aerosol OT™ or AOT) during stirring (and voltex) after adding a crosslinker which reacts with the carboxyl groups (diamines or $CaCl_2$)). The microparticles were collected by a centrifuging and washing process. In that regard, and without limitation to any mechanism, spherical microparticles are formed in the solution. After, crosslinking, when solvent is removed, the spheres contract and form a hollow core. In a number of embodiments, diamines are used for crosslinking the carboxyl groups or $CaCl_2$ may be used for crosslinking (ionic crosslinking).

Figure 22B:
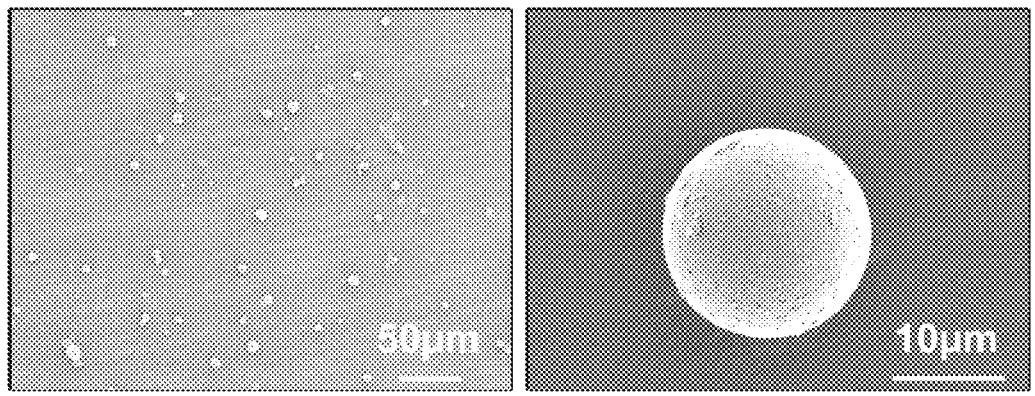
FIG. 22B illustrates photomicrographs of microparticles of PSBEU-COOH loaded with paclitaxel at two levels of magnification.
Figure 22C:
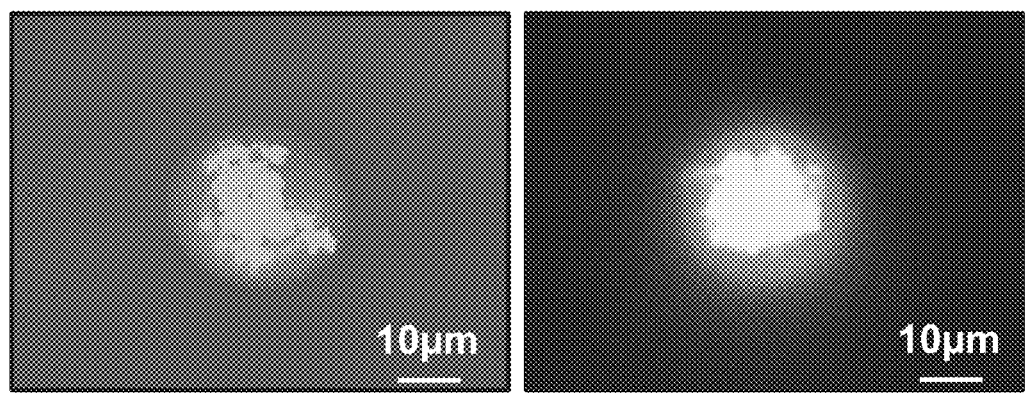
FIG. 22C illustrates confocal microscope images of OREGON GREEN® paclitaxel (a fluorescent paclitaxel derivative available from Molecular Probes, Inc. of Eugene, Oreg.) loaded and rhodamine stained PSBEU-COOH particles.

The microparticles were observed by a SEM after a dehydration process with EtOH solution. The size of obtained PSBEU-COOH micro-particles was variable between approximately 5 to 30 μm and showed void structure (see FIG. 22B) which could be used as a drug carrier. The anti-proliferation drug paclitaxel was loaded in PSBEU-COOH microparticles, and the microparticles could be immobilized on, for example, Mg alloy surfaces by physical or chemical tethering (for example, via methods as illustrated in FIG. 25A through D discussed below). FIG. 22C illustrates confocal microscope images of OREGON GREEN® paclitaxel loaded and rhodamine stained PSBEU-COOH particles. FIGS. 23A and B illustrate an albumin-FITC loaded PSBEU-COOH microparticle prepared by a double emulsion system (that is, using two baths of 2,2,2-trifluoroethanol/AOT and water/polyvinyl alcohol, subsequently) without a cross-linker. Carboxyl groups thus remain available on the surface of microparticle (for example, for use in the further applications) as illustrated in FIG. 24.

In that regard, FIG. 24 illustrates an idealized, schematic illustration of a microparticle of PSBEU-COOH polymer loaded with a drug such as paclitaxel (represented as cross-hatched circles). In the illustrated embodiment, no crosslinking has occurred or carboxyl/COOH groups remain after crosslinking as described above. A ratio of crosslinking compound functionality (for example, a low molecular weight diamine) to COOH functionality may be chosen such that not all COOH functionality is exhausted in the crosslinking reaction. In all biodegradable polymers hereof, whether formed as microparticles or otherwise, functional groups such as COOH groups on the polymer can be used to covalently tether the polymer to a surface via reaction of the functional groups of the biodegradable polymer with functional groups on the surface which are reactive with the functional groups of the biodegradable polymer. Functional groups other than COOH on the biodegradable polymer hereof may also be used in a crosslinking reaction for microparticles hereof. Suitable functional groups for the biodegradable polymers hereof include carboxyl groups, alkyl siloxanes (—SiOR, wherein R is an alkyl group such as a $C_1$-$C_{12}$ alkyl group), thiol groups, and amine groups. Such reactive functional group may for example be incorporated into the polymer in the manner described above for carboxyl groups. Protective groups, as known in the chemical arts, may be used in some embodiments to protect such functional group during formation of the biodegradable polymers hereof.

Figure 25A:
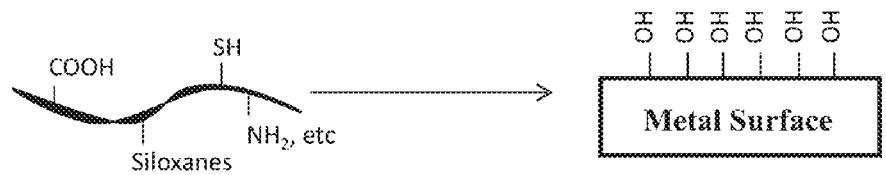
FIG. 25A illustrates tethering of a biodegradable polymer hereof with a surface via reaction of functional groups on the biodegradable polymer with functional groups on the surface.
Figure 25B:
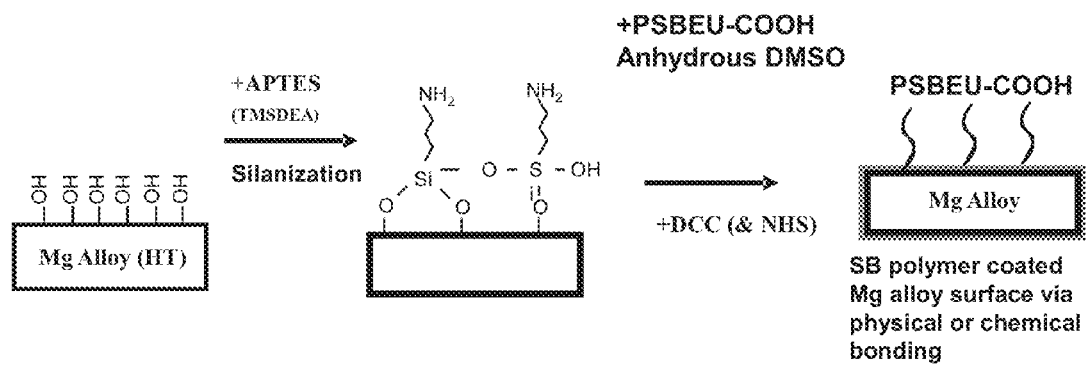
FIG. 25B illustrates tethering of a biodegradable polymer hereof with a surface via reaction of functional groups on the biodegradable polymer with functional groups on an intermediate or mediator that has been tethered to the surface via silanization.
Figure 25C:
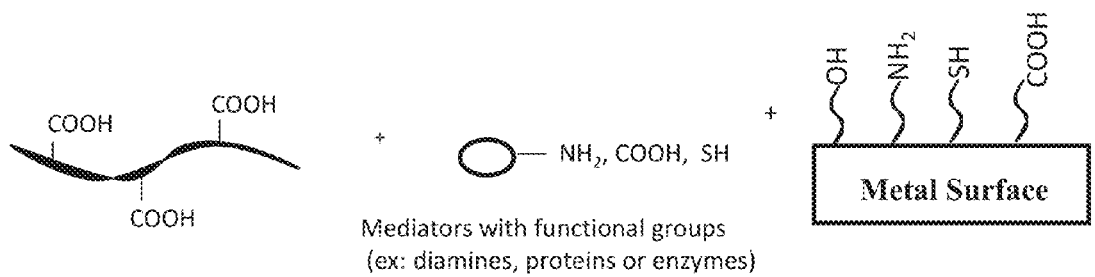
FIG. 25C illustrates tethering of a biodegradable polymer hereof with a surface via reaction of functional groups on the biodegradable polymer with functional groups on a surface introduced via functionalization of the surface of via an intermediate or mediator that has been tethered to the surface.
Figure 25D:
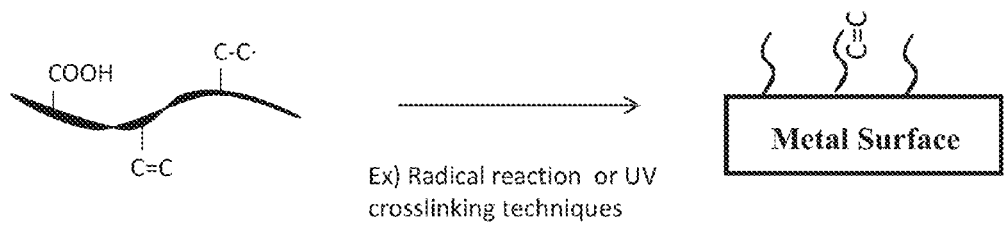
FIG. 25D illustrates tethering of a biodegradable polymer hereof with a surface via reaction of functional groups on the biodegradable polymer which can form a radical.

In the representative example of carboxyl functional groups on the biodegradable polymers hereof tethered to a metal oxide surface such as the surface of a Mg alloy stent, the carboxyl groups can be reacted directly with hydroxyl groups on the surface via a condensation reaction. FIG. 25A illustrates representative examples of functional groups on a biodegradable polymer hereof which can be reacted with functional groups (for example, hydroxyl groups) of a surface such as a metal surface. Alternatively, in the case of carboxyl and/or other functional groups on the biodegradable polymers hereof, a surface can be functionalized for reaction with those functional groups or an intermediate may be tethered to the surface for reaction with the functional groups of the biodegradable polymer. For example, in FIG. 25B, a surface of an article is modified via silanization to introduce —$NH_2$ groups, which are then reacted with the functional groups of the biodegradable polymer (for example, carboxyl groups). Use of various intermediates/mediators or functionalized surfaces for attachment of a biodegradable polymer hereof is further illustrated in FIG. 25C. As illustrated in FIG. 25D, functional group which are able to form a radical (for example, upon application of energy such as UV energy) can be used to tether a biodegradable polymer hereof to a surface. In a number of embodiments, a surface may undergo plasma treatment to prepare the surface for such tethering. Although representative examples of metal surfaces are used herein, the polymers hereof can be tethered to any surface including appropriate functionality.

EXPERIMENTAL

Materials.

Polycaprolactone diol (PCL, Mn=2000, Sigma) and dimethylolpropionic acid (DMPA, sigma) were dried in a vacuum oven at 60° C. overnight to remove residual water before synthesis. 1,4-Diisocyanatobutane (BDI, Sigma) and putrescine (Sigma) were purified using vacuum distillation before usage. Stannous octotate (Sn(Oct)2, Sigma) was dried using 4 A molecular sieves. 1,1,1,6,6,6-Hexafluoroisopropanol (HFIP, Oakwood, Inc), dimethylsulfone (DMSO, Sigma), lipase from *Thermomyces lanuginosus* (≥100000 U/g, Sigma), dicyclohexylcarbodiimide (DCC, Sigma), cysteamine (Sigma), dimethylolpropionic acid (DMPA, Sigma), benzophenone (Sigma), and paclitaxel (TAXOL, LC Laboratories, Inc.) were used as received. 2-Methacryloyloxyethyl phosphorycholine (MPC) was a gift from Prof. Kazuhiko Ishihara at the University of Tokyo. Sulfobetaine diol (SB-diol) was synthesized from 1,3-propane sultone and N-butyldiethanolamine in methylene chloride at 40° C. for 15 h. Other chemical agents were purchased from Sigma.

Synthesis of Aminated Phosphorycholine (PC-$NH_2$).

Functional phosphorycholine (PC) molecules with amino groups (PCNH2) were synthesized under UV irradiation by thiol-ene reaction (FIG. 1A). 14 The synthesis procedure was as follows: a roundbottom flask equipped with a magnetic stirrer was charged with anhydrous methanol (10 mL) after adding MPC (10 mM final concentration), cysteamine (11 mM final concentration), and benzophenone as a catalyst. After argon injection for 5 min to remove the air, the flask containing the reaction mixture was sealed and placed under a high intensity UV lamp (UVP Model B 100AP, Upland, CA) at a 15 cm gap at room temperature for 3 h. Anhydrous dimethyl ether/chloroform mixed solvent (50/50) was used to precipitate the product and remove the unreacted monomer after excess solvent was evaporated from the reactive bath using a rotary evaporator. The obtained product was dried in a vacuum oven. The chemical structure of PC-NH2 was confirmed by 1H NMR. For PC-NH2 (in $CDCl_3$), the peaks were: δ (ppm) 1.26-1.28 (α-$CH_3CH$), 1.55-1.65 (1.26-1.28 (α-$CH_3$)), 2.22-2.51 (SCH_2CH), 2.54-2.64 ($CH_2CH_2S$), 2.81-2.91 ($CH_2NH_2$), 2.80 (3.01 ($CH_2NH_2$)), 3.28-3.43 ($CH_2N(CH_3)_3$), 3.70-3.83 ($CH_2N(CH_3)_3$), 4.01-4.15 ($OCH_2$), 4.19-4.41 ($CH_2PO_4CH_2$, 4H). The PC-$NH_2$ was successfully purified, and monomer peaks at both 5.61-5.75 and 6.02-6.12 ppm (C=C) were not observed on the NMR spectrum.

Synthesis of Poly(ester urethane) Urea with Carboxyl Groups (PEUU-COOH).

PEUU-COOH was synthesized from a soft segment of PCL and dimethylolpropionic acid DMPA blend, a hard segment BDI, and a chain extender putrescine (FIG. 1B). PCL and DMPA were dissolved in DMSO in a three-necked flask with argon protection and stirring at 70° C., followed by BDI and Sn(Oct)$_2$ catalyst (3 drops) addition. The PCL:DMPA molar ratio was 70:30. After 3 h, the prepolymer solution was cooled to room temperature, then putrescine/DMSO solution was added dropwise to the prepolymer solution. The molar ratio of (PCL+DMPA)/BDI/putrescine was 1:2:1 and the final polymer solution concentration was approximately 4%. The reaction continued overnight with stirring at room temperature. The polymer was precipitated in deionized water, rinsed using ethanol, and then dried in a vacuum oven at 60° C. for 3 d. The yield of PEUU-COOH was above 90%. Control PEUU was synthesized from a soft segment PCL alone. PEUU and PEUU-COOH films were fabricated by solvent casting using HFIP, following drying in a vacuum oven at 60° C. for 3 d.

Synthesis of Poly(ester urethane) Urea with Phosphorylcholine Groups (PEUU-PC).

PEUU-PC was obtained by grafting aminated phosphorycholine into PEUU-COOH through a condensation reaction between carboxyl and amino groups (FIG. 1B). Specifically, PEUU-COOH was completely dissolved in agitated DMSO solvent at 70° C. and then cooled to room temperature. An excess amount of PC-$NH_2$ was dissolved in DMSO and then added to the PEUU-COOH/DMSO solution, following addition of an excess amount of DCC. The reaction continued at room temperature overnight. For polymer precipitation, the polymer solution was poured into ethylene ether, and then an excess of deionized water was added to precipitate the polymer. The polymer was rinsed 3× using deionized water and then 100% ethanol 2× to completely remove unreacted PC-NH$_2$. The final product was dried in a vacuum oven at 60° C. for 3 d. The PEUU-PC yield was approximately 75%. PEUU-PC films were obtained using solvent casting in HFIP, as described above.

Synthesis of Polyurethane Ureas Containing Sulfobetaine (PCSUU).

Polycaprolactone (PCL, Mn=2000) and sulfobetaine-diol (SB-diol) were mixed at a molar ratio of 100/0, 75/25, 50/50, 25/75 or 0/100 in a 3-necked flask, and dried by azeotropic distillation in toluene following dimethylsulfone (DMSO) addition. Diisocyanatobutane was charged under argon and 0.5 wt % Sn(Oct)$_2$ was added. After 3 h reaction at 70° C., a putrescine/DMSO solution was added dropwise. The reaction continued overnight and the polymer was precipitated in H$_2$O. The final product was immersed in isopropanol for 6 h and dried in a vacuum oven at 60° C. for 3 d with a yield>90%. Films were cast from hexafluroisopropanol (HFIP) solutions.

Fabrication of Paclitaxel-Loaded Films.

Polyurethane and paclitaxel (5 wt % to polymer) were dissolved in HFIP to obtain a 5% (w/v) solution, and then the mixture was poured into a Teflon dish. After complete solvent evaporation at room temperature, the paclitaxel-loaded film was dried in a vacuum oven at room temperature for 2 d, and then stored in a freezer at −20° C. for further testing. For all samples, the same amount of polymer and drug was used.

Polymer Characterization.

Polymer chemical structure was characterized by 1H nuclear magnetic resonance (1H NMR, 300 MHz, Bruker Biospin Co., Billerica, Mass.) using DMSO-d6 solvent and/or FTIR. Polymer surface composition was analyzed by X-ray photoelectron spectroscopy (XPS) using a Surface Science Instruments S-probe spectrometer with a takeoff angle of 55° (performed at NESAC-BIO, Univ. of Washington). The surface composition of a given sample was averaged from two composition spots and one high resolution C is analysis. The mean value for three different samples was determined. The water contact angle of the polymer film surface in air was measured using a sessile drop method on a UCA contact angle instrument (UCA optima, AST Products Inc.; n=12 per polymer). Thermal properties were measured by differential scanning calorimetry (DSC, DSC-60, Shimazu) at a scanning range of −100 to 200° C. at a heating rate of 20° C./min with a nitrogen flow.

A 2×20 mm strip was cut from the polymer film and its mechanical properties were measured on an MTS Tytron 250 MicroForce Testing Workstation at room temperature with a crosshead speed of 25 mm/min according to ASTM D638-98. Four samples were tested for each polymer.

Polymer degradation behavior was evaluated by weight loss after hydrolytic and enzymatic degradation. For hydrolysis, the weighed polymer film (W$_0$) was immersed in 10 mL of PBS at 37° C. At each time point, the sample was rinsed with deionized water 3× and dried in a vacuum oven at 60° C. for 3 d, followed by weighing (W$_1$). For enzymatic degradation, the weighed polymer film (W$_0$) was placed in 2 mL of 100 U lipase/PBS solution loaded in a 20 mL glass vial, and then the glass vial was immersed in a water bath at 37° C. The fresh lipase/PBS solution was replaced twice per week. At each time point, the sample was rinsed 3× using deionized water, dried in a vacuum oven at 37° C. for 3 d, and then weighed (W$_1$). The mass remaining was calculated as W1/W0×100%. Three samples were used for each polymer at each time point.

Thermal properties were detected using differential scanning calorimetry. Water absorption was recorded after 24 h PBS immersion at 37° C. Protein adsorption was determined using a model protein, fibrinogen, and a micro-BCA assay.

Ovine Blood Contact.

Whole ovine blood was collected by jugular venipuncture using an 18 gauge 1½" needle directly into a syringe containing heparin (3.0 U/mL) after discarding the first 3 mL for blood contacting experiments. NIH guidelines for the care and use of laboratory animals were observed, and all animal procedures were approved by the Institutional Animal Care and Use Committee (IACUC) at the University of Pittsburgh. Previous reports from our group using this withdrawal technique from acclimated sheep showed that the platelets obtained were highly responsive to agonist stimulation in vitro. 15,16 The polymer surfaces were assessed for surface thrombotic deposition in vitro by employing a simple rocking test 17 with heparinized ovine blood (heparin 3.0 U/mL) and incubated for a period of time (for example, 2 h or 3 h) at 37° C. on a hematology mixer (Fisher Scientific, Pittsburgh, Pa.). After ovine blood contact, surfaces were gently rinsed with PBS and immersed in a 2.5% glutaraldehyde solution for 2 h at 4° C. to fix the surface adherent platelets, and treated for 1 h in 1% (w/v) OsO4. The samples were serially dehydrated with increasing ethanol solutions and then sputter-coated with gold/palladium. Each sample surface was observed by scanning electron microscopy (SEM; JSM-6330F, JEOL USA, Inc., Peabody, Mass.). Deposited platelets on each surface were quantified by a lactate dehydrogenase (LDH) assay 17 with an LDH Cytotoxicity Detection Kit (Clontech Laboratories, Inc. Mountain View, Calif.).

Paclitaxel Release Profile Measurement.

Samples cut from paclitaxel-loaded films were weighed and then immersed in 10 mL of 10% (v/v) ethanol/PBS solution at 37° C. Release measurements were performed under sink conditions. At each defined time point, the 10 mL releasate solution was collected and 10 mL of fresh 10% ethanol/PBS solution was added. Four separate samples were used for each polymer type. The paclitaxel in the collected releasate was detected at 230 nm using an ultraviolet spectrometer (Perkin-Elmer UV/vis Lambda 40, U.S.A.). A standard curve was obtained from a series of known concentrations of paclitaxel ethanol/PBS solutions.

Rat Vascular Smooth Muscle Cell Growth Inhibition.

A series of 6 mm diameter discs were punched from paclitaxel-loaded films using a standard punch. The samples were sterilized under 30 min of UV irradiation, then directly immersed into a well (24-well cell culture plate), which was preseeded with 5×103 rat vascular smooth muscle cells (rSMCs) with 2 mL of cell culture medium (DMEM supplemented with 10% fetal bovine serum and 1% penicillin/streptomycin solution). The cell culture medium was exchanged every 3 d. A control group included cells cultured in wells without the addition of the paclitaxel-loaded disk. A mitochondrial activity assay (MTT; Sigma) was conducted to measure rSMC metabolic activity. For each group, four samples were used in parallel. A live/dead kit (Invitrogen Inc.) was also employed to stain rSMCs at each time point, and fluorescent images were taken using an Olympus fluorescent microscope to visualize relative cell numbers and to detect dead cells. A control group of PEUU without paclitaxel loading was not included in this work because previous reports have shown the ability of this surface to support cell growth without toxicity.

Statistical Analysis.

All results are represented as mean±standard deviation. The data were analyzed by one-way ANOVA, followed by posthoc Neuman-Keuls testing. $P<0.05$ was considered to represent a significant difference. Repeated measures ANOVA was used for polymer degradation and drug release comparisons using IBM SPSS Statistics, version 20.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of forming an implantable article, comprising: providing a biodegradable polymer comprising anti-thrombogenic zwitterionic groups at least one of within a backbone of the biodegradable polymer or pendant upon the backbone of the biodegradable polymer, biodegradable groups in the backbone of the biodegradable polymer and a plurality of functional groups reactive with reactive functional groups on a surface of the implantable article; and reacting at least a portion of the plurality of functional groups with the reactive functional groups on the surface of the implantable article to covalently bond the biodegradable polymer to the implantable article.

2. The method of claim 1 wherein the biodegradable groups include at least one hydrolytically labile bond.

3. The method of claim 1 wherein the biodegradable groups comprise at least one of ester groups, anhydride groups, amide groups, carbonate groups, orthoester groups, or thioether-ester groups.

4. The method of claim 3 wherein the biodegradable groups comprise ester groups.

5. The method of claim 1 wherein the anti-thrombogenic groups comprise at least one of a phosphorylcholine group, a derivative of a phosphorylcholine group, a sulfobetaine group, a derivative of a sulfobetaine group, a carboxybetaine group, or a derivative of a carboxybetaine group.

6. The method of claim 1 wherein the biodegradable polymer is a thermoplastic elastomer.

7. The method of claim 6 wherein the biodegradable polymer comprises at least one of urethane or urea linkages.

8. The method of claim 7 wherein the biodegradable polymer is a polyurethane or a polyurethane urea comprising soft segments.

9. The method of claim 8 wherein the biodegradable polymer is formed by first forming a precursor polymer via the reaction of:
(a) a multi-functional active hydrogen component comprising a polymer comprising multiple active hydrogen functional groups and biodegradable groups in the backbone thereof and at least one compound comprising multiple active hydrogen functional groups and at least one of the plurality of functional groups, and
(b) a multi-functional isocyanate component; and
reacting the precursor polymer with a compound comprising at least one zwitterionic group and a functional group reactive with one of the plurality of functional groups.

10. The method of claim 9 wherein the polymer comprising multiple active hydrogen functional groups and biodegradable groups in the backbone thereof is a polyester.

11. The method of claim 9 wherein the biodegradable polymer is formed via the reaction of the multi-functional active hydrogen component comprising the polymer comprising multiple active hydrogen functional groups and biodegradable groups in the backbone thereof, the at least one compound comprising multiple active hydrogen functional groups and the at least one of the plurality of functional groups and a compound comprising at least one zwitterionic group and multiple active hydrogen functional groups with a multi-functional isocyanate component.

12. The method of claim 11 wherein the polymer comprising multiple active hydrogen functional groups and biodegradable groups in the backbone thereof is a polyester.

13. The method of claim 1 wherein at least one of the plurality of functional groups of the biodegradable polymer comprise at least one of a carboxyl group, an amine group, a thiol group, an alkyl siloxane group.

14. The method of claim 1 wherein the plurality of functional groups of the biodegradable polymer comprise carboxyl groups.

15. The method of claim 1 further comprising forming the biodegradable polymer into microparticles.

16. The method of claim 15 wherein a portion of the plurality of functional groups of the biodegradable polymer are reacted with a crosslinking compound comprising at least two functional groups reactive with at least two of the plurality of functional groups of the biodegradable polymer after the microparticles are formed.

17. The method of claim 1 wherein the implantable article is a stent and the biodegradable polymer is a coating on the stent.

18. The method of claim 1 wherein the implantable article is a scaffold for tissue engineering.

19. The method of claim 1 wherein the biodegradable polymer further comprises a biologically active agent releasably loaded within the biodegradable polymer.

20. The method of claim 19 wherein the biologically active agent is selected from the group consisting of an anti-proliferative agent, an antibiotic, an antiviral, an anti-mycotic, an anticancer agent, an immunosuppressant, a chemotherapeutic agent, an anti-rejection agent, an analgesic agent, and an anti-inflammatory agent.

21. The method of claim 19 wherein the biologically active agent is an anti-proliferative agent.

22. An implantable article, comprising: a biodegradable polymer comprising anti-thrombogenic groups comprising zwitterionic groups at least one of in a backbone of the biodegradable polymer or pendant upon the backbone of the biodegradable polymer and biodegradable groups in the backbone of the biodegradable polymer, the biodegradable polymer being covalently bonded to a surface of the implantable article.

23. A method of forming an implantable article, comprising: forming the implantable article from a biodegradable polymer comprising anti-thrombogenic zwitterionic groups at least one within a backbone of the biodegradable polymer or pendant upon the backbone of the biodegradable polymer and biodegradable groups in the backbone of the biodegradable polymer.

24. The method of claim 23 wherein the anti-thrombogenic groups comprise at least one of a phosphorylcholine group, a derivative of a phosphorylcholine group, a sulfobetaine group, a derivative of a sulfobetaine group, a carboxybetaine group, or a derivative of a carboxybetaine group.

25. The method of claim 23 wherein the biodegradable polymer is a thermoplastic elastomer.

26. The method of claim 25 wherein the biodegradable polymer comprises at least one of urethane or urea linkages.

27. The method of claim 26 wherein the biodegradable polymer is a polyurethane or a polyurethane urea comprising soft segments.

28. The method of claim 23 further comprising forming the biodegradable polymer into microparticles.

29. The method of claim 28 wherein the biodegradable polymer further comprises a plurality of functional groups and the method further comprises reacting the biodegradable polymer with a crosslinking compound comprising at least two functional groups reactive with at least two of the plurality of functional groups of the biodegradable polymer after the microparticles are formed.

* * * * *